United States Patent
Zhou

(10) Patent No.: US 10,870,690 B2
(45) Date of Patent: Dec. 22, 2020

(54) PROTEIN THERAPEUTANT AND METHOD FOR TREATING CANCER

(71) Applicant: Yihong Zhou, Irvine, CA (US)

(72) Inventor: Yihong Zhou, Irvine, CA (US)

( * ) Notice: Subject to any disclaimer, the term of this patent is extended or adjusted under 35 U.S.C. 154(b) by 53 days.

(21) Appl. No.: 15/609,370

(22) Filed: May 31, 2017

(65) Prior Publication Data
US 2017/0267747 A1    Sep. 21, 2017

Related U.S. Application Data

(63) Continuation-in-part of application No. 14/771,983, filed as application No. PCT/US2014/032597 on Apr. 1, 2014, now Pat. No. 9,676,834.

(60) Provisional application No. 62/375,196, filed on Aug. 15, 2016, provisional application No. 61/807,445, filed on Apr. 2, 2013.

(51) Int. Cl.
C07K 14/78    (2006.01)
A61K 38/00    (2006.01)

(52) U.S. Cl.
CPC .............. *C07K 14/78* (2013.01); *A61K 38/00* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 5,595,756 A * | 1/1997 | Bally | A61K 9/1272 264/4.1 |
| 6,593,104 B1 | 7/2003 | Stone et al. | |
| 2002/0156263 A1 | 10/2002 | Chen et al. | |
| 2004/0191819 A1 | 9/2004 | Eveleigh et al. | |
| 2006/0094054 A1 | 5/2006 | Schiemann et al. | |
| 2016/0009775 A1 | 1/2016 | Zhou | |

FOREIGN PATENT DOCUMENTS

WO    2012159085    11/2012

OTHER PUBLICATIONS

Bowie et al. (Science, 1990, 247:1306-1310) (Year: 1990).*
Burgess et al. (J. Cell Biol. 111:2129-2138, 1996) (Year: 1990).*
Lazar et al. (Mol. Cell. Biol., 8:1247-1252, 1988) (Year: 1988).*
Bork (Genome Research, 2000,10:398-400) (Year: 2000).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042 (Year: 1997).*
Jain RK (Scientific American, Jul. 1994,58-65) (Year: 1994).*
Seeliger et al Mol Cancer Res 2009;7(2) (Year: 2009).*
Abnova datasheet for EFEMP1 (downloaded Oct. 13, 2018 from http://www.abnova.conn/products/products_detail.asp?catalog_id=H00002202-P01) (Year: 2018).*
Clustal Omega Alignment (performed Oct. 13, 2018 at https://www.ebi.ac.uk/Tools/services/web/toolresult.ebi?jobId=clustalo-l20181013-220651-0438-30426986-p2m) (Year: 2018).*
Yuan et al. "Isolation of cancer stem cells from adult glioblatoma multiforme," Oncogene, Dec. 16, 2004, vol. 23, pp. 9392-9400.
Hu et al., "Fibulin-3 Promotes Glioma Growth and Resistance through a Novel Paracrine Regulation of Notch Signaling", Cancer Res; 72(15):3873-3885, (Aug. 1, 2012).
Hu et al., "EFEMP1 suppresses malignant glioma growth and exerts its action within the tumor extracellular compartment", 2011, Mol Cancer, 10:123, pp. 1-12.
Hu et al., "Cell context-dependent dual effects of EFEMP1 stabilizes subpopulation equilibrium in responding to changes of in vivo growth environment", 2015, Oncotarget, 6(31): 30762-30772.
Hu et al., "Anti-EGFR function of EFEMP1 in glioma cells and patient prognosis", 2014, Oncoscience, 1(3): 205-15.
Hu et al., "Tumor-Specific Chromosome Mis-Segregation Controls Cancer Plasticity by Maintaining Tumor Heterogeneity", 2013, PLoS One, 8(11): e80898; pp. 1-16.
Zhou et al., "Weaponizing human EGF-containing fibulin-like extracellular matrix protein 1 (EFEMP1) for 21st century cancer therapeutics", Oncoscience, 2016; 3(7-8): 208-219.

* cited by examiner

*Primary Examiner* — Brian Gangle
*Assistant Examiner* — Andrea K McCollum
(74) *Attorney, Agent, or Firm* — Riverside Law LLP

(57) ABSTRACT

The present invention relates to compositions for treating cancer by having one or more activities of inhibiting cancer growth, inhibiting cancer cell invasion, and inhibiting cancer recurrence.

9 Claims, 16 Drawing Sheets

Specification includes a Sequence Listing.

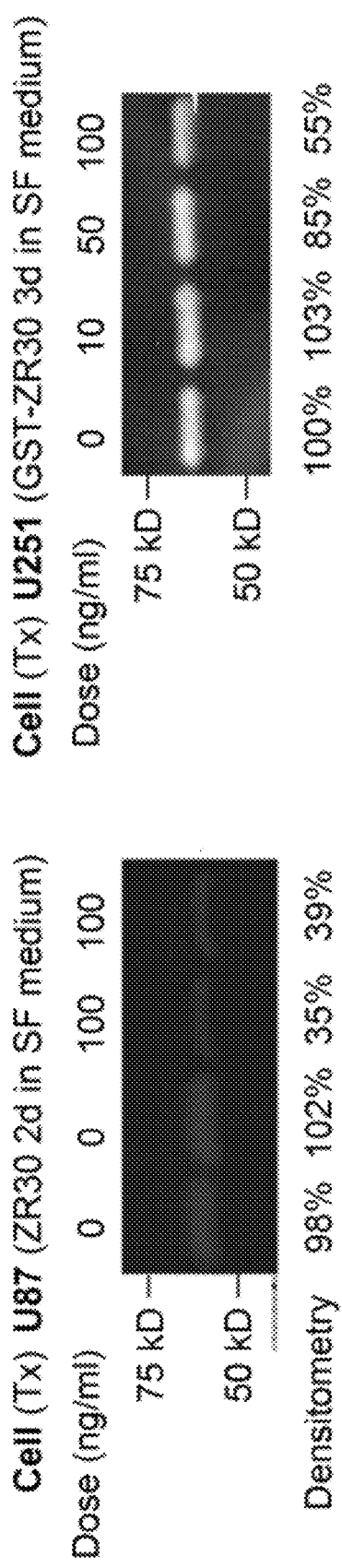
Figure 8A
Figure 8B
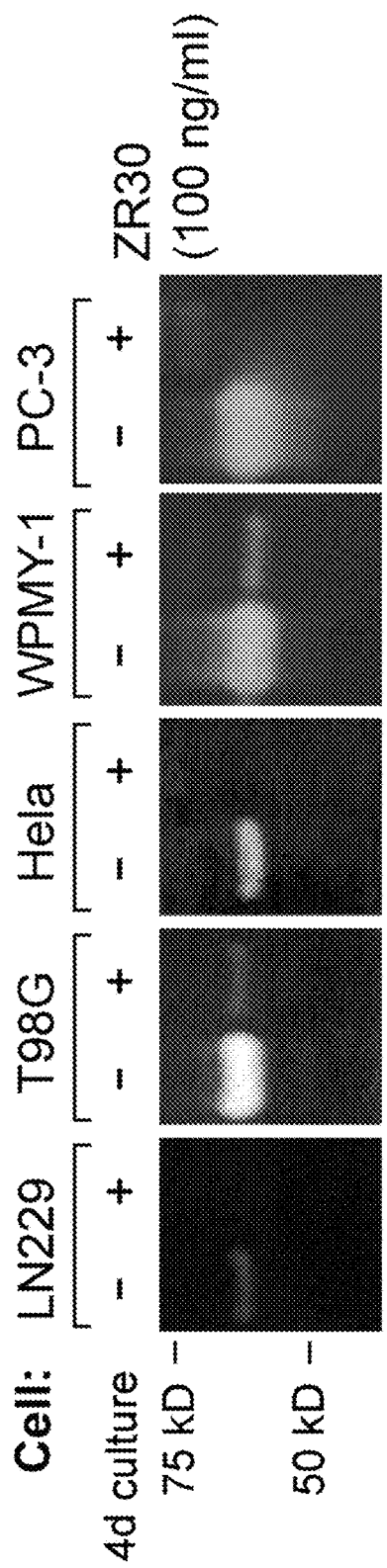
Figure 8C

PROTEIN THERAPEUTANT AND METHOD FOR TREATING CANCER

CROSS-REFERENCE TO RELATED APPLICATIONS

The present application claims priority under 35 U.S.C. § 119(e) to U.S. Provisional Patent Application No. 62/375,196, filed Aug. 15, 2016, and is a continuation-in-part of, and claims priority to U.S. patent application Ser. No. 14/771,983, filed Sep. 1, 2015, which is the U.S. national phase application filed under 35 U.S.C. § 371 claiming benefit to International Patent Application No. PCT/US2014/032597, filed Apr. 1, 2014, which is entitled to priority under 35 U.S.C. § 119(e) to U.S. Provisional Patent Application No. 61/807,445, filed Apr. 2, 2013, each of which applications is hereby incorporated by reference in its entirety.

BACKGROUND OF THE INVENTION

Fibulins are a seven-member family of secreted glycoproteins characterized by possessing repeated epidermal growth-factor-like domains and a unique C-terminal structure. Studies of fibulin protein function in cancer indicate that some fibulin proteins have tumor-suppressor activity and some have oncogenic activity. Moreover, some individual fibulin proteins (e.g., fibulin 3/EFEMP1) demonstrate tumor suppressor activity or oncogenic activity in a tissue-specific manner.

EFEMP1 tumor suppressor function is evident. EFEMP1 has an anti-angiogenic function via suppression of endothelial cell sprouting. EFEMP1 overexpression inhibits tumorigenicity of fibrosarcoma cells. Reduced EFEMP1 expression and/or EFEMP1 promoter methylation occurs in lung, liver, breast, colon, prostate, and nasopharyngeal carcinoma. EFEMP1 expression in glioblastoma multiforme, hepatocellular, and nasopharyngeal carcinoma is correlated with a favorable prognosis. EFEMP1 suppresses AKT signaling activity in nasopharyngeal carcinoma and glioblastoma cell lines.

EFEMP1 oncogenic function is also evident. Elevated EFEMP1 expression has been correlated to poor prognosis for cervical cancer. The results of a clinical trial demonstrated that EFEMP1 over-expression was correlated to poor prognosis for breast carcinoma. In pancreatic adenocarcinoma cells, EFEMP1 over-expression promotes xenograft formation. EFEMP1 activates AKT signaling activity in pancreatic carcinoma cell lines. In certain glioma cells, EFEMP1 has been shown to enhance in vitro substrate-specific cell adhesion and promote cell motility and dispersion.

The deadly form of brain cancer, glioblastoma multiforme (GBM), for which there is not yet any effective treatment, is made up of disparate subpopulations of cells characterized by having distinct proliferation and infiltration properties. The mechanism underlying GBM recurrence after treatment, such as surgery, radiation, and chemotherapy, has not been conclusively identified. It has been speculated that recurrence is caused by an infiltrative subpopulation of GBM cells that have neural stem cell properties (so-called tumor stem cells) and are resistant to radiation and chemotherapy. GBM growth appears largely dependent on an angiogenic tumor microenvironment, and anti-angiogenic therapies have been shown to temporarily repress GBM tumor growth. But anti-angiogenic therapies do not improve overall survival of GBM patients and result in tumor recurrence with an increased pattern of infiltration. Previously, a therapy targeting glioma cell infiltration has been lacking.

Available data regarding the evolution of cancer point towards chromosome instability, intra-tumoral heterogeneity (or tumor heterogeneity) and the tumor microenvironment as the three most important factors leading to the changes and the fundamental modification needed to break through normal physiological barriers and trigger neoplastic transformation (Merlo et al., 2006, Nat Rev Cancer, 6(12): 924-935, Marusyk et al., 2010, Biochim Biophys Acta, 1805(1): 105-117, Hu et al., 2013, PLoS One, 8(11): e80898). The development of new cancer therapeutants should reflect the deep understanding of these three facets and their interplay.

EGF-containing fibulin-like extracellular matrix protein one (EFEMP1), also known as fibulin-3, has been demonstrated to counter cancer growth. EFEMP1 is one of the most commonly reported, tumor-specific, extracellular matrix proteins; a secreted glycoprotein that forms intramolecular bridges within the extracellular matrix to mediate cellular processes and tissue remodeling. Tumor suppression functions of EFEMP1 have been demonstrated in the extracellular matrix (Hu et al., 2011, Mol Cancer, 10:123). Dual functions of EFEMP1 in two cell subpopulations, non-stem like tumor-mass-forming cells (TMC) and stem-like tumor initiating cells (STIC) from a single glioblastoma multiforme (GBM) tumor has also been demonstrated (Hu et al., 2015, Oncotarget, 6(31): 30762-30772).

The failure to successfully treat cancer such as GBM during advanced stages is due to the lack of understanding between the interplay among tumor cell subpopulations and the tumor microenvironment. Thus there is a need in the art for improved compositions and methods for treating cancer. The present invention addresses this unmet need.

SUMMARY OF THE INVENTION

In one aspect, the invention provides an isolated polypeptide that comprises: an amino acid sequence having at least about 90% identity with the amino acid sequence set forth in SEQ ID NO:14.

In one embodiment, the isolated polypeptide comprises an amino acid sequence having at least about 95% identity with the amino acid sequence set forth in SEQ ID NO:14. In one embodiment, the isolated polypeptide comprises the amino acid sequence set forth in SEQ ID NO:14.

In another aspect, the invention provides a method for treating cancer in a subject, comprising administering to the subject a therapeutically effective amount of a composition comprising an isolated polypeptide comprising an amino acid sequence selected from the group: a) an amino acid sequence having at least 90% identity to SEQ ID NO:14; b) an amino acid sequence having at least 95% identity to SEQ ID NO: 1 wherein the amino acid at position 218 relative to SEQ ID NO: 1 is aspartic acid; and c) an amino acid sequence having at least 95% identity to SEQ ID NO: 2, wherein the amino acid at position 210 relative to SEQ ID NO: 2 is aspartic acid.

In one embodiment, the method results in at least one activity selected from the group consisting of inhibition of cancer cell invasion, inhibition of cancer cell growth and inhibiting cancer cell recurrence.

In one embodiment, the cancer is characterized as being associated with activation of at least one selected from the group consisting of EGFR, NOTCH, AKT and extracellular matrix metallopeptidases.

In one embodiment, the cancer is selected from the group: a low grade glioma, a medium grade glioma, a high grade glioma, a fibrosarcoma, a colorectal cancer, a lung cancer, a colon cancer, a liver cancer, a breast cancer, a prostate cancer, a pancreatic cancer, a skin cancer, a cervical cancer, a kidney cancer, a gastric cancer, and a nasopharyngeal cancer multiforme. In one embodiment, the cancer is a glioma. In one embodiment, the cancer is a glioblastoma multiforme.

In one embodiment, a therapeutically effective amount of the composition is administered to a subject by intra-tumoral injection.

In another aspect, the invention provides an isolated nucleic acid molecule comprising a nucleotide sequence encoding a peptide comprising an amino acid sequence having at least about 90% identity with the amino acid sequence set forth in SEQ ID NO:14.

In one embodiment, the isolated nucleic acid molecule comprises a nucleotide sequence having at least about 90% identity with the nucleotide acid sequence set forth in SEQ ID NO:23. In one embodiment, the isolated nucleic acid molecule comprises a nucleotide sequence having at least about 95% identity with the nucleotide acid sequence set forth in SEQ ID NO:23. In one embodiment, the isolated nucleic acid molecule comprises the nucleotide sequence of SEQ ID NO:23.

In another aspect, the invention provides a method for treating cancer in a subject, comprising administering to the subject a therapeutically effective amount of a composition comprising at least one nucleic acid molecule comprising a nucleotide sequence encoding a peptide comprising an amino acid sequence selected from the group: a) an amino acid sequence having at least 90% identity to SEQ ID NO:14; b) an amino acid sequence having at least 95% identity to SEQ ID NO: 1 wherein the amino acid at position 218 relative to SEQ ID NO: 1 is aspartic acid; and c) an amino acid sequence having at least 95% identity to SEQ ID NO: 2, wherein the amino acid at position 210 relative to SEQ ID NO: 2 is aspartic acid.

In one embodiment, the nucleic acid molecule comprises at least one nucleic acid molecule comprising a nucleotide sequence having at least about 90% identity with the nucleotide acid sequence set forth in SEQ ID NO:23.

BRIEF DESCRIPTION OF THE DRAWINGS

The following detailed description of exemplary embodiments of the invention will be better understood when read in conjunction with the appended drawings. For the purpose of illustrating the invention, there are shown in the drawings embodiments which are presently exemplary. It should be understood, however, that the invention is not limited to the precise arrangements and instrumentalities of the embodiments shown in the drawings.

FIG. 1A is a CLUSTAL W amino acid sequence alignment of fibulin proteins EFEMP1, EFEMP2, and fibulin 5 (FBLN5). FIG. 1B is a CLUSTAL W amino acid sequence alignment of an EGFR-homologous region (EHR) in human, mouse, and rat EFEMP1 protein, four isoforms of human EGFR protein, and a deletion mutant of EGFR.

FIG. 4B is a plot of cell invasion from the MATRIGEL® invasion assay described in Example 5, initiated with neural sphere cultures of U251 cells infected with the E1, E2, E5, 13, E15, and E18 pTRIPZ lentiviral constructs described in FIG. 2 and Example 1 and vector pTRIPZ (Vec).

FIG. 7A is an image of a SDS-PAGE gel stained by Coomassie Blue that showed >95% purity of 38.61 kDa ZR30. FIG. 7B is an image of an immunoblot with the EFEMP1 antibody detecting the ZR30 protein. Positive control was a cell lysate of EFEMP1 transfected 293T.

FIG. 8A through FIG. 8C are a set of images depicting the results of a Gelatin Zymography assay for detecting ZR30-treated glioma cells. FIG. 8A and FIG. 8B, demonstrates equal amounts of conditioned medium protein (FIG. 8A; 1 μg for U87) (FIG. 8B; 4 μg for U251) analyzed for glioma cells after culturing in basal media for 2-3 days with or without addition of ZR30 to a final concentration of 50-100 ng/ml. The ZR30-mediated inhibition of MMP2 activation was observed in other human cell lines of GBM (LN229 and T98G), cervical cancer (Hela), prostate cancer stroma (WPMY-1) and metastatic prostate cancer (PC-3) (FIG. 8C).

FIG. 9A is an image demonstrating 4-day U251 cell cultures with or without ZR30 followed by a 2-day culture in serum-free medium, along with a densitometry plot of U251 immunoblots. FIG. 9B is an image demonstrating 2-day U251-NS cell cultures with or without ZR30 prior to removal of GST. FIG. 9C is an image demonstrating 3-day U251 cell cultures with or without ZR30, followed by a 2-day culture in serum-free medium with or without 30 min exposure to EGF. FIG. 9D is an immunoblot demonstrating that AKT phosphorylation was upregulated in response to a 30-min exposure to EGF along with a reduction of EGFR, which are indexes for EGF-mediated activation of EGFR signaling. FIG. 9E is an immunoblot demonstrating ZR30's capacity to disable the glioblastoma cells' ability to respond to EGF in activating EGFR/AKT signaling, seen in another human cell line of GBM (T98G) and metastatic prostate cancer (PC-3) (lanes 5 and 11), compared to the control (lanes 4 and 10). Here an increase of NOTCH1 expression was observed (normalized to ACTB) in response to EGF in T98G, which was disabled by ZR30 (lanes 4 and 5). PC-3 does not express NOTCH1, hence no such effect was seen.

FIG. 10A is an image illustrating the comparison of human SPAG16 to mouse Spag16 gene copy number ratios of individual mouse brains from PBS or ZR30-treated mice. FIG. 10B is an image illustrating the comparison of GFP to RFP copy number ratios in DNA samples described in FIG. 10A, which corresponds to ratio of GFP-transfected U251 and RFP-transfected U251-NS cell numbers. The bar heights and error bars are averages and 95% confidence intervals. Significant Bonferroni-adjusted P values from comparisons to the PBS-control are shown.

FIG. 11A is an image illustrating the comparison of mouse survival from i.t. injection of 5 µl PBS or ZR30 (70 ng/µl) 10 days post i.c. tumor cell implantation, with median (SEM) survival 40.5 (4.2) and 57.8 (2.1) days, respectively. FIG. 11B, is an image illustrating the comparison of mouse survival from i.t. injection of 10 µl PBS or ZR30 (70 ng/µl) 21 days post i.c. implantation, with median (SEM) survival 57 (1.6) and 74.5 (5.5) days, respectively.

DETAILED DESCRIPTION

Figure 2:
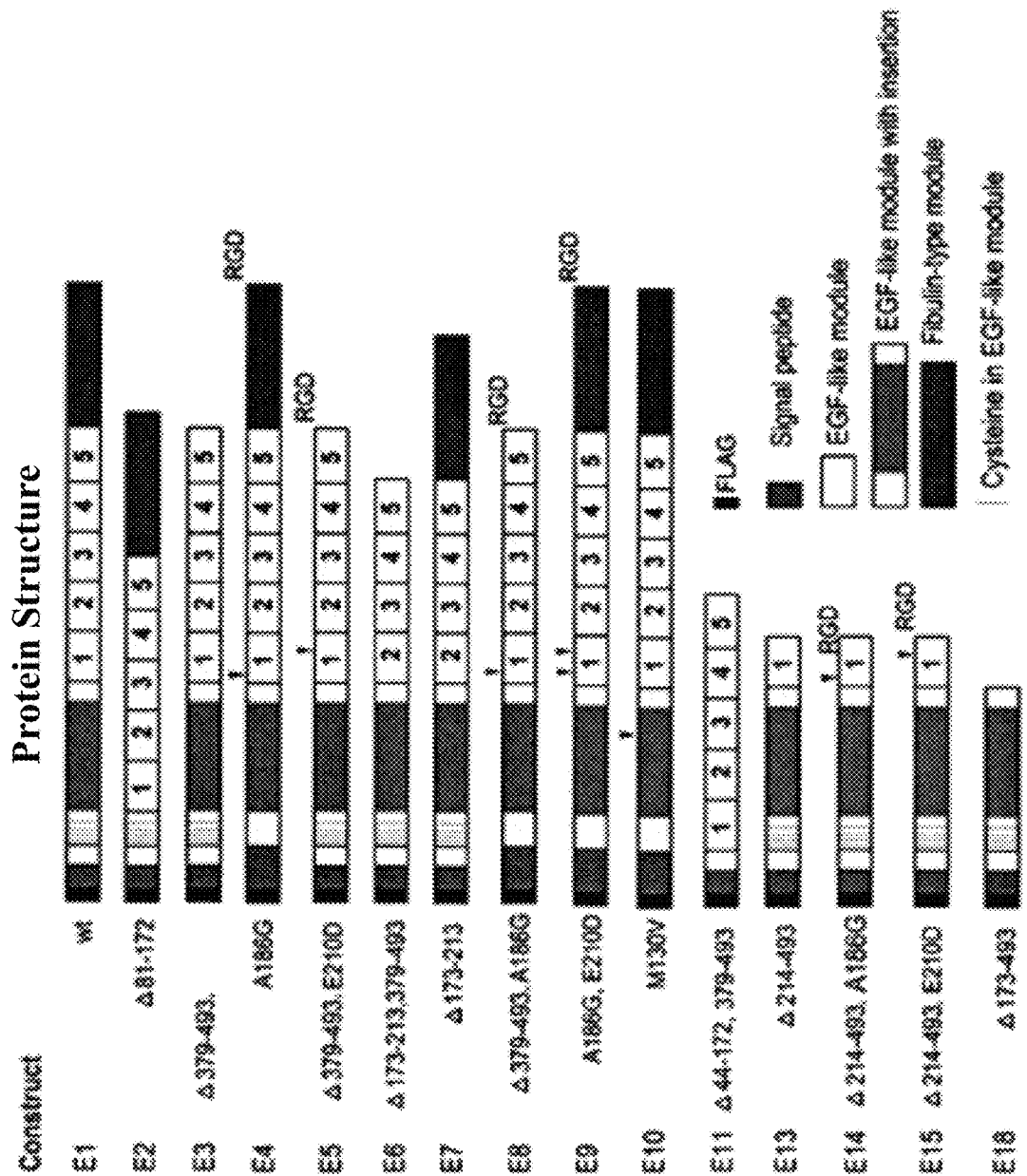
FIG. 2 is a schematic of the modular structure of a FLAG-tagged, wild-type EFEMP1 protein construct E1 and a panel of FLAG-tagged, EFEMP1 protein variant constructs E2-E11, E13-E15, and E18.

The present invention relates in part to compositions and methods for treating or preventing cancer. In certain aspects, the composition comprises a peptide useful for inhibiting cancer growth, inhibiting cancer cell infiltration, inhibiting cancer recurrence, or a combination thereof. In certain embodiments, the peptide is useful for the treatment of glioma (e.g., a glioblastoma multiforme).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "treat," as used herein, means reducing the frequency and/or severity of a sign or symptom of a disease or disorder experienced by a subject. Thus, "treat" and "treating" are not limited to the case where the subject (e.g., patient) is cured and the disease or disorder is eradicated. Rather, the present invention also contemplates treatment that merely reduces signs or symptoms, improves (to some degree) and/or delays disease or disorder progression. The term "treatment" also refers to the alleviation, amelioration, and/or stabilization of signs or symptoms, as well as a delay in the progression of signs or symptoms of a disease or disorder. As used herein, to "alleviate" a disease or disorder means to reduce the frequency and/or severity of one or more signs and/or symptoms of the disease or disorder.

The term "effective amount" in a subject, as used herein, refers to an amount that provides a therapeutic or prophylactic benefit in the subject. The term "therapeutically effective amount" refers to the amount of the compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the signs and/or symptoms of the disease or disorder being treated. The therapeutically effective amount will vary depending on the compound, the disease or disorder, the severity of the disease or disorder, and the age, weight, etc., of the subject to be treated.

A "therapeutic" treatment is a treatment administered to a subject who exhibits signs of pathology, for the purpose of diminishing or eliminating those signs.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intramuscular, intracerebral, intra-tumoral, and convection enhanced delivery.

The terms "patient," "subject," "individual," and the like are used interchangeably herein, and refer to any animal, or cells thereof whether in vitro or in situ, amenable to the methods described herein. In some embodiments, patient, subject or individual is a mammal such as a non-primate (e.g., cows, pigs, horses, cats, dogs, rats, etc.) and a primate (e.g., monkey and human). In certain non-limiting embodiments, the patient, subject or individual is a human.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron (s).

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

An object achieved by the present invention is to provide amino acid sequences of EFEMP1 polypeptide variants that possess at least one activity of inhibiting cancer growth, inhibiting cancer cell infiltration, and inhibiting cancer recurrence, such as a glioma (e.g., a glioblastoma multiforme). In some embodiments, amino acid sequence variants of wild-type EFEMP1 protein, at times referred to as EFEMP1 derived tumor suppressor proteins (ETSP), inhibit proliferation and invasion activities of fast proliferative and invasive glioma tumor cell subpopulations separately and together in orthotopic tumor formatting. Such ETSPs have been discovered, at least in part, by amino acid sequence homology studies of wild-type EFEMP1 and experimentation with variant EFEMP1 polypeptides.

Figure 1A:
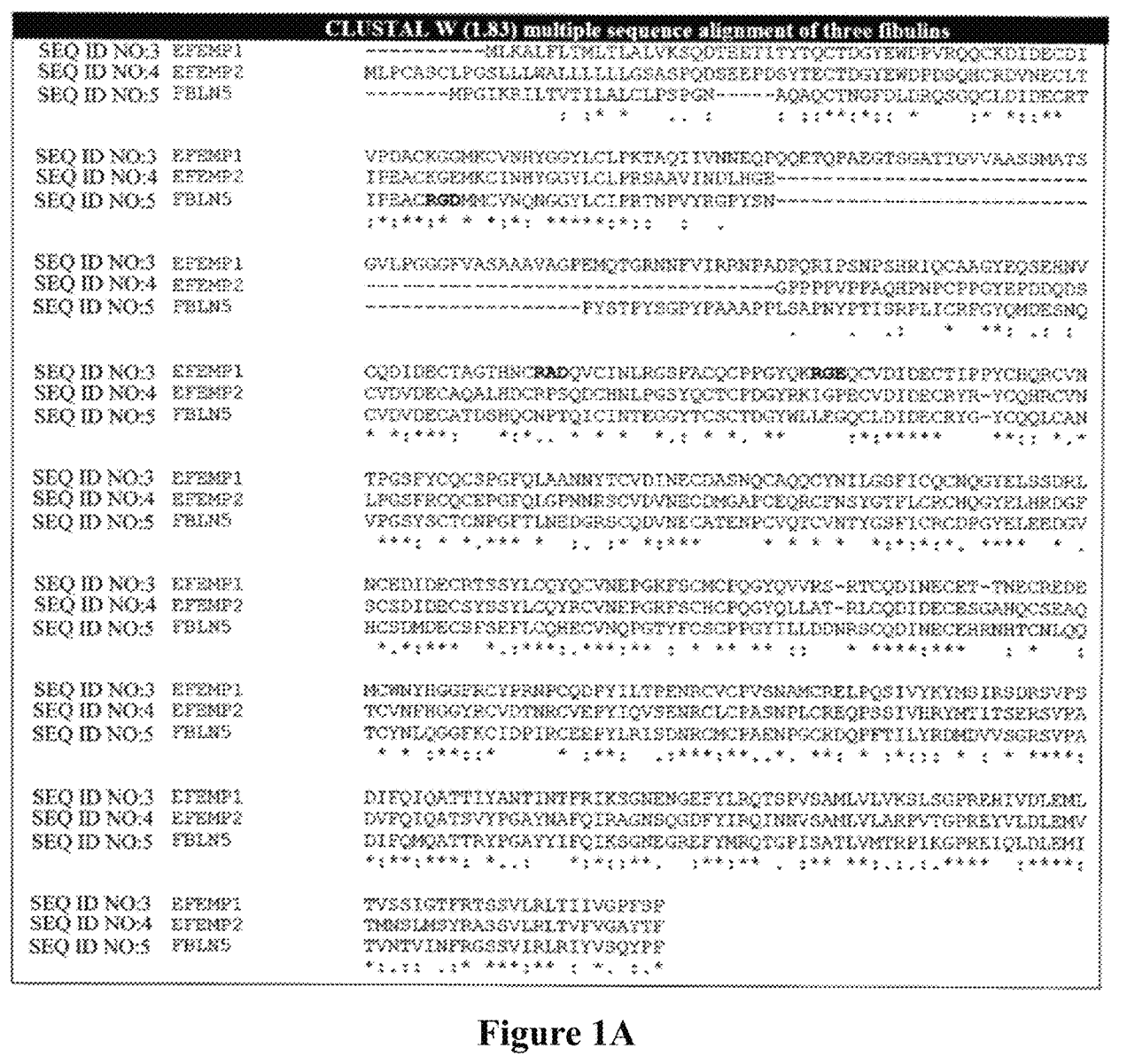
Figure 1B:
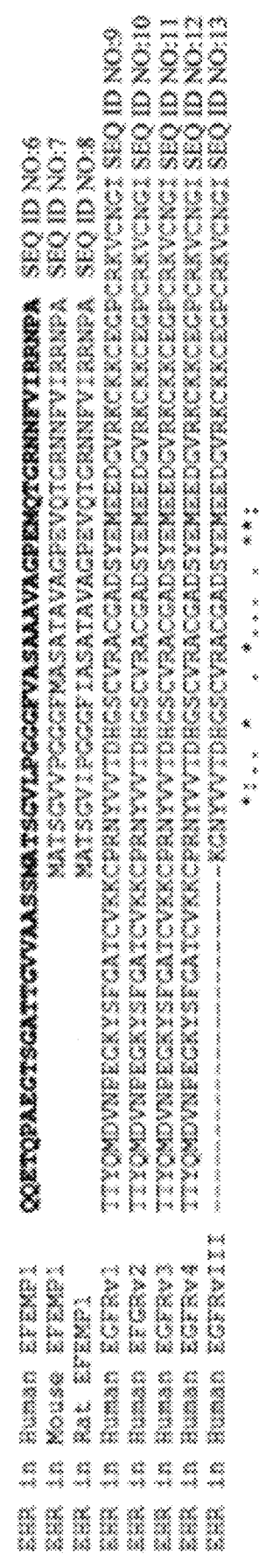

FIG. 1A is a CLUSTAL W (1.83) alignment of the amino acid sequences of wild-type EFEMP1, EFEMP2, and fibulin 5 (FBLNS) which shows that, although EFEMP1 is a longer protein than EFEMP2 and FBLNS, a high degree of sequence similarity exists among those proteins. FIG. 1A also shows the location of weak (RGE) and strong (RGD) integrin binding sites in wild-type EFEMP1 and FBLNS, respectively. FIG. 1B is a CLUSTAL W (1.83) alignment of a 38-amino acid EGFR-homologous region (EHR) in EFEMP1. The aligned EHR amino acid sequences are: human, mouse, and rat EFEMP1; four isoforms of human EGFR (EGFRv1, EGFRv2, EGFRv3, EGFRv4); and a deletion mutant of EGFR (EGFRvIII) identified in human cancers.

FIG. 2 is a schematic of modular domains present in a panel of FLAG-tagged, EFEMP1 proteins encoded by constructs E1-E11, E13-E15, and E18. Construct E1 encodes a full-length EFEMP1 protein having wild-type (wt) amino acid sequence, which includes a signal peptide, a DSL motif, an EGF-like module with an insertion, five EGF-like modules numbered 1-5, and a fibulin-type module.

Construct E2 encodes an EFEMP1 variant in which amino acids 81-172 have been deleted, largely eliminating the EFEMP1-specific, EGF-like module with an insertion of wt EFEMP1.

Construct E3 encodes an EFEMP1 variant in which amino acids 379-493 have been deleted, largely eliminating the fibulin-type module of wt EFEMP1.

Construct E4 encodes an EFEMP1 variant in which amino acid 186 has been changed from Alanine to Glycine, which converts a weak integrin binding site of wt EFEMP1 into a strong integrin binding site.

Construct E5 encodes an EFEMP1 variant in which amino acids 379-493 have been deleted, largely eliminating the fibulin-type module of wt EFEMP1, and in which amino acid 210 has been changed from glutamic acid to aspartic acid, converting a weak integrin binding site of wt EFEMP1 into a strong integrin binding site.

Construct E6 encodes an EFEMP1 variant in which amino acids 173-213 and 379-493 have been deleted, largely eliminating the EGF-like module 1 and the fibulin-type module of wt EFEMP1.

Construct E7 encodes an EFEMP1 variant in which amino acids 173-213 have been deleted, largely eliminating EGF-like module 1 of wt EFEMP1.

Construct E8 encodes an EFEMP1 variant in which amino acids 379-493 have been deleted, largely eliminating the fibulin-type module of wt EFEMP1, and in which amino acid 186 has been changed from Alanine to Glycine, which converts a weak integrin binding site of wt EFEMP1 into a strong integrin binding site.

Construct E9 encodes an EFEMP1 variant in which amino acid 186 has been changed from Alanine to Glycine, amino acid 210 has been changed from glutamic acid to aspartic acid, converting two weak integrin binding sites of wt EFEMP1 into two strong integrin binding sites.

Construct E10 encodes an EFEMP1 variant in which amino acid 130 has been changed from Methionine to Valine, converting that amino acid residue in human wt EFEMP1, positioned in a 20-amino acid sequence in the EGF-like module with insertion that shares sequence similarity to EGFR, to the corresponding mouse and rat EFEMP1 residue.

Construct E11 encodes an EFEMP1 variant in which amino acids 44-172 and 379-493 have been deleted, partly eliminating the DSL motif of wt EFEMP1 and largely eliminating the EGF-like module with insertion and the fibulin-type module of wt EFEMP1.

Construct E13 encodes an EFEMP1 variant in which amino acids 214-493 have been deleted, largely eliminating the EGF-like modules 2-5 and the fibulin-type module of wt EFEMP1.

Construct E14 encodes an EFEMP1 variant in which amino acids 214-493 have been deleted, largely eliminating EGF-like modules 2-5 and the fibulin-type module of wt EFEMP1, and in which amino acid 186 has been changed from Alanine to Glycine, converting a weak integrin binding site of wt EFEMP1 into a strong one.

Construct E15 encodes an EFEMP1 variant in which amino acids 214-493 have been deleted, largely eliminating EGF-like modules 2-5 and the fibulin-type module of wt EFEMP1, and in which amino acid 210 has been changed from Glutamic Acid to Aspartic Acid, converting a weak integrin binding site of wt EFEMP1 into a strong one.

Construct E18 encodes an EFEMP1 variant in which amino acids 173-493 have been deleted, largely eliminating EGF-like modules 1-5 and the fibulin-type module of wt EFEMP1.

U251 is a high-tumorigenicity malignant glioma cell line derived from human glioblastoma multiforme. Different protocols exist for culturing U251. Parental culture of U251 is serum-containing and adherent. Neural sphere (NS) culture of U251 is serum-free and non-adherent, or fibronectin-anchored adherent, with supplements used for culture of normal neural stem cells. U251 is composed of disparate subpopulations of cells. In parental culture, the majority cell subpopulation carries two normal copies of chromosome 7 and one 7q-deleted copy of chromosome 7. In NS culture, the majority cell subpopulation carries one normal copy of chromosome 7 and one 7q-deleted copy of chromosome 7.

U251 cells that carry two normal copies of chromosome 7 and one 7q-deleted copy of chromosome 7 show fast proliferation in the S.C. xenograft assay described in Example 4. They also are also lacking in invasiveness, but form the bulk of the tumor mass, in the I.C. xenograft assay described in Example 8.

U251-NS cells that carry one normal copy of chromosome 7 and one 7q-deleted copy of chromosome 7 show high levels of invasiveness in the MATRIGEL® invasion and zymography assays described in Examples 5 and 6. They also possess tumor stem-like cell features and are lacking in tumorigenicity in the S.C. xenograft assay described in Example 4. U251-NS cells transfected to overexpress vascular endothelial growth factor form tumors in subcutaneous (S.C.) xenograft assay described in Example 4. U251-NS cells forms highly invasive tumor in intracranial (I.C.) xenograft assay described in Example 8. And they are more invasive than U251 cells that carry two normal copies of chromosome 7 and one 7q-deleted copy of chromosome 7 in the IC xenograft assay described in Example 8.

Table 1 reports qRT-PCR results obtained with three types of U251 cell cultures. The first type was parental culture of U251 cell lines stably transfected with the E1, E2, E3, E4, E5, E6, E7, E8, E9, E10, E11, E13, E14, E15 and E18 pcDNA 3.1+ constructs described in FIG. 2 and Example 1 and with plasmid vector pcDNA 3.1+(Vec). The second type was parental culture of U251 cells infected with the E1, E2, E5, E6, E7, E8, E11, E13, E15, and E18 pTRIPZ lentiviral constructs described in FIG. 2 and Example 2 and with plasmid vector pTRIPZ (Vec). The third type was neural sphere culture of U251 (U251-NS) cells infected with the E1, E2, E3, E5, E7, E8, E10, E11, E13, E15, and E18 pTRIPZ lentiviral constructs described in FIG. 2 and Example 2 and with plasmid vector pTRIPZ (Vec). The forward primer of the PCR primer pair annealed to the FLAG tag and the reverse primer annealed to exon 4 of EFEMP1. The results of Table 1 indicate that the E1, E2, E3, E4, E5, E6, E7, E8, E9, E10, E11, E13, E14, E15 and E18 constructs are expressed in parental cultures of U251 transfectant cells. The results of Table 1 also indicate that the E1, E2, E5, E6, E7, E8, E11, E13, E15, and E18 constructs are expressed in parental cultures of U251 lentiviral infectant cells, in a doxycycline-inducible manner. They also indicate that the E1, E2, E3, E5, E7, E8, E10, E11, E13, E15, and E18 constructs are expressed in doxycycline containing neural sphere cultures of U251 (U251-NS) lentiviral infectant cells.

TABLE 1

| | FLAG-EFEMP1/ACTB * 1000 | | | |
|---|---|---|---|---|
| | Cell | | | |
| | U251 pcDNA | U251 pTRPZ lentiviral infectant | | U251-NS |
| Construct | transfectant | (−) Dox | (+) Dox | (+) Dox |
| Vector | | 0.0 | 0.0 | 0.1 |
| E1 | 1.6 | 0.1 | 12.7 | 133.3 |
| E2 | 23.7 | 0.1 | 3.4 | 74.2 |
| E3 | 81.0 | NE | N/E | 46.7 |
| E5 | 22.4 | 0.1 | 4.5 | 1.9 |
| E6 | 29.6 | 0.1 | 8.1 | |

TABLE 1-continued

FLAG-EFEMP1/ACTB * 1000

| | Cell | | | |
|---|---|---|---|---|
| | U251 pcDNA | U251 pTRPZ lentiviral infectant | | U251-NS |
| Construct | transfectant | (−) Dox | (+) Dox | (+) Dox |
| E7 | 1.8 | 0.0 | 3.3 | 43.8 |
| E8 | 1.6 | 0.1 | 5.2 | 14.2 |
| E9 | 1.4 | N/E | N/E | N/E |
| E10 | 49.5 | N/E | N/E | 55.2 |
| E11 | 153.9 | 0.1 | 54.9 | 198.0 |
| E13 | 24.2 | 0.1 | 25.4 | 6.6 |
| E15 | 62.5 | 0.1 | 9.3 | 85.4 |
| E18 | N/E | 0.2 | 6.9 | 142.3 |

N/E: Not examined

Table 2 reports results obtained with the anchorage-independent growth and cell proliferation soft agar colony formation assay described in Example 3, initiated with parental cultures of U251 cell lines stably transfected with the E1, E2, E3, E4, E5, E6, E7, E8, E9, E10, E11, E13, E14, and E15 pcDNA 3.1+ constructs described in FIG. 2 and Example 1 and with plasmid vector pcDNA 3.1+ (Vec). Table 2 also reports results obtained with the anchorage-independent growth and cell proliferation soft agar colony formation assay described in Example 3, initiated with neural sphere cultures of U251 cells (U251-NS) infected with the E1, E2, E5, E7, E8, E10, E11, E13, E15, and E18 pTRPZ lentiviral constructs described in FIG. 2 and Example 2 and with plasmid vector pTRIPZ (Vec). Lentivial infectants were cultured in medium containing doxycycline to induce transgene expression, and expression was verified by assaying RFP expression with a fluorescent microscope. The results of Table 2 indicate that EFEMP1 protein variants expressed from constructs E2, E5, E6, E7, E8, E11, E13, E14, and E15 suppress U251 and/or U251-NS cell growth. They also indicate that EFEMP1 protein variant E3 increased cell proliferation in the U251 soft agar assay.

TABLE 2

| | U251 | | U251-NS | |
|---|---|---|---|---|
| Construct | Size | Number (Ave, SD) | Size | Number (Ave, SD) |
| Vec | 3+ | 1.0, 1.3 | 2+ | 1.0, 0.1 |
| E1 | 3+ | 1.1, 0.4 | 1+ | 0.6, 0.2 |
| E2 ✓ | 3+ | 0.6, 0.2 | 1+ | 1.4, 0.2 |
| E3 | 6+ | 0.7, 0.1 | | |
| E4 | 3+ | 1.0, 0.2 | | |
| E5 ✓ | 3+ | 1.1, 0.4 | 1+ | 0.5, 0.1 |
| E6 ✓ | 1+ | 0.2, 0.1 | | |
| E7 ✓ | 1+ | 0.7, 0.3 | 1+ | 0.5, 0.2 |
| E8 ✓ | 3+ | 1.3, 0.4 | 1+ | 0.6, 0.1 |
| E9 | 3+ | 1.1, 0.1 | | |
| E10 | 4+ | 0.7, 0.1 | 2+ | 1.0, 0.2 |
| E11 ✓ | 1+ | 0.3, 0.1 | 1+ | 0.8, 0.2 |
| E13 ✓ | 3+ | 1.6, 0.2 | 1+ | 0.7, 0.2 |
| E14 ✓ | 3+ | 0.6, 0.2 | | |
| E15 ✓ | 3+ | 0.5, 0.1 | 1+ | 1.7, 0.3 |
| E18 | | | 2+ | 1.5, 0.2 |

Figure 3A:
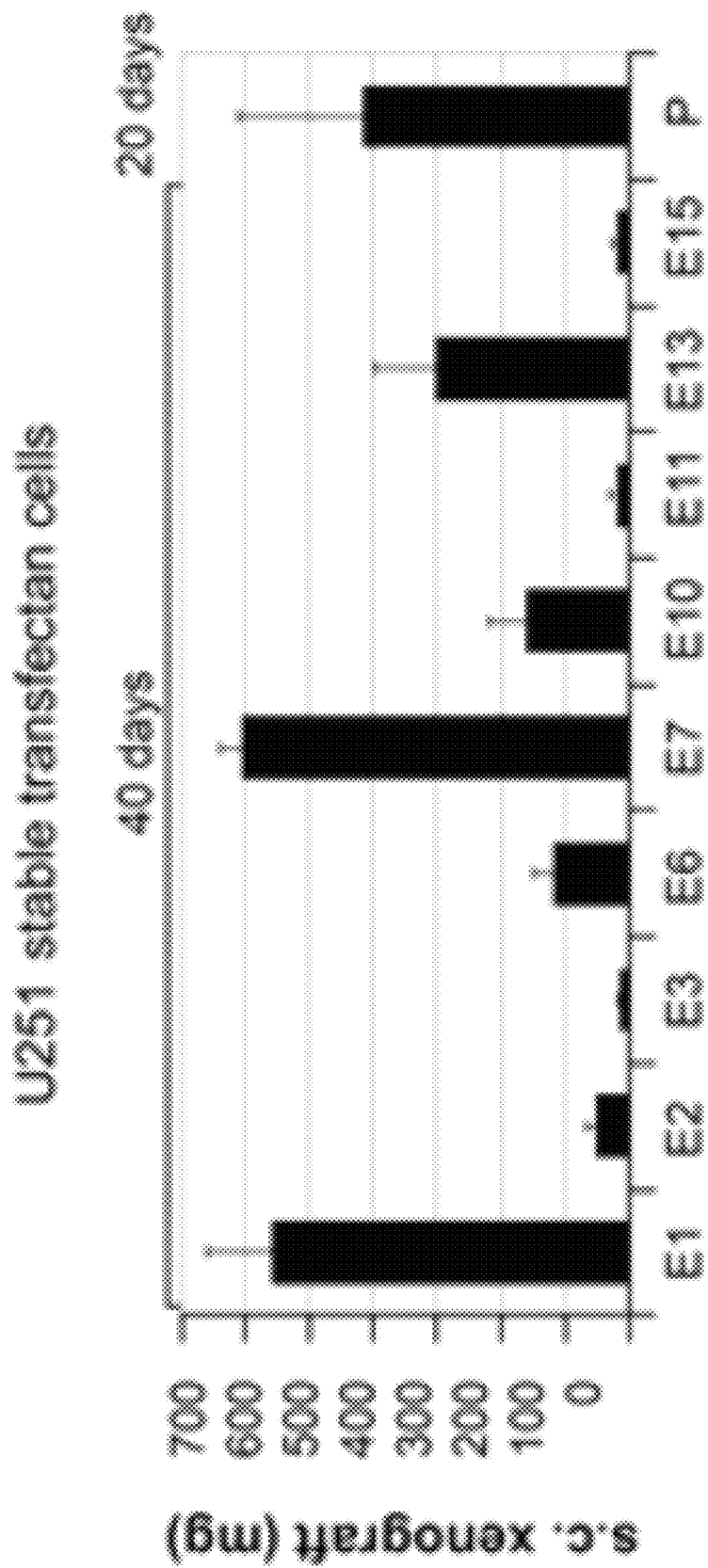
FIG. 3A is a plot of tumor weights from the S.C. xenograft assay described in Example 4, initiated with parental cultures of U251 cell lines stably transfected with the E1-E3, E6-E7, E10-E11, E13, and E15 pcDNA 3.1+ constructs described in FIG. 2 and Example 1 and vector pcDNA 3.1+(P).

FIG. 3A is a plot of tumor weights from the S.C. xenograft assay described in Example 4, initiated with parental cultures of U251 cell lines stably transfected with the E1, E2, E3, E6, E7, E10, E11, E13, and E15 pcDNA 3.1+ constructs described in FIG. 2 and Example 1 and with U251 parental control cells (P). The results indicate that the EFEMP1 protein variants expressed from constructs E2, E3, E5, E6, E11, and E15 suppress U251 cells forming tumors in the S.C. xenograft assay.

Figure 3B:
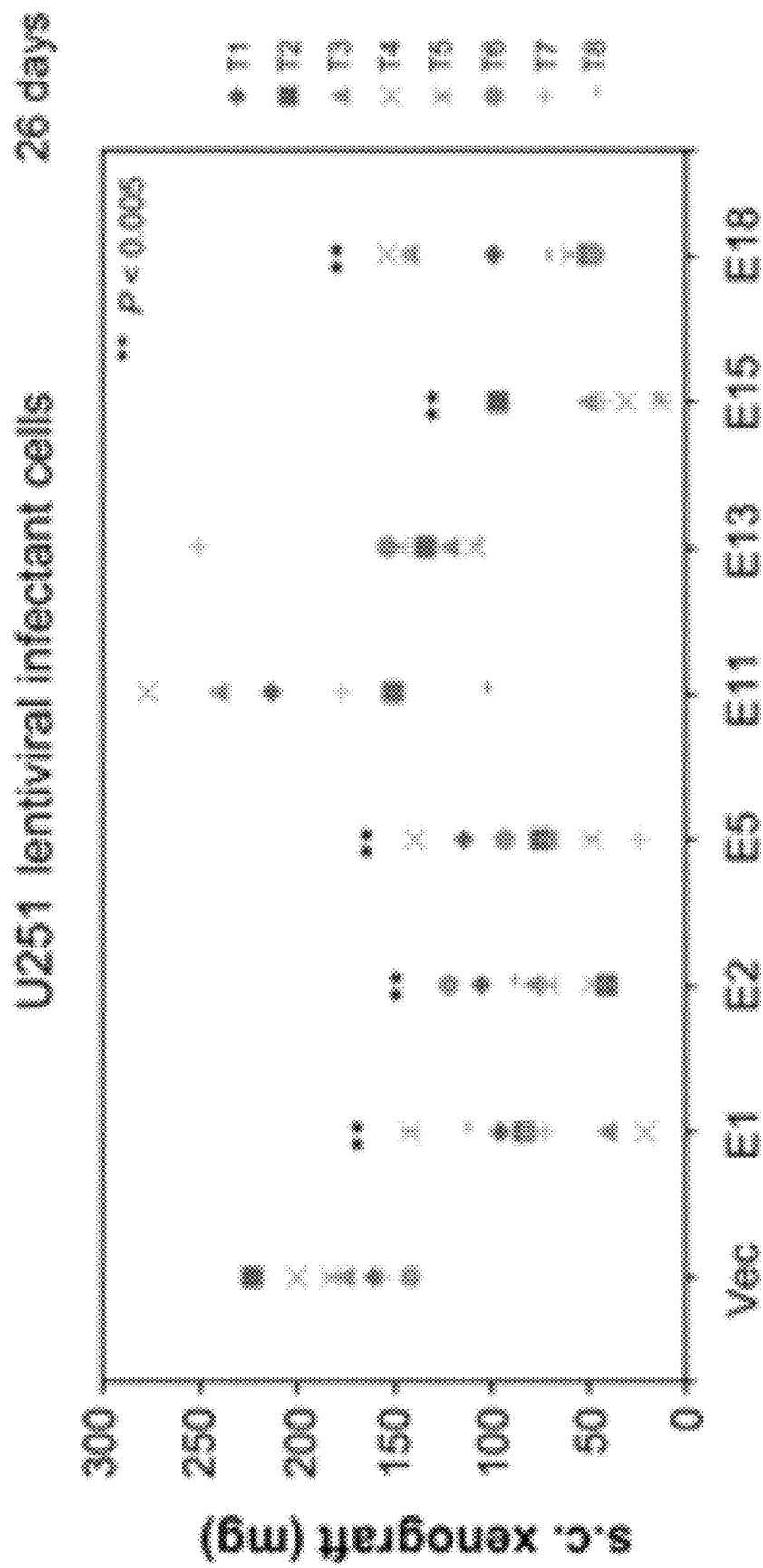
FIG. 3B is a plot of tumor weights from the S.C. xenograft assay described in Example 4, initiated with parental cultures of U251 cells infected with the E1, E2, E5, E11, E13, E15, and E18 pTRIPZ lentiviral constructs described in FIG. 2 and Example 1 and vector pTRIPZ (Vec).

FIG. 3B is a plot of tumor weights from the S.C. xenograft assay described in Example 4, initiated with parental cultures of U251 cells infected with the E1, E2, E5, E11, E13, E15, and E18 pTRIPZ lentiviral constructs described in FIG. 2 and Example 2 and with plasmid vector pTRIPZ (Vec). Mice were fed with doxycycline-containing water from day 1 and throughout the experiment. RFP-expression was shown in the resulting tumors. The results indicate that the EFEMP1 protein variants expressed from constructs E2, E5, E15, and E18 suppress U251 cells forming tumors in the S.C. xenograft assay.

Figure 4A:
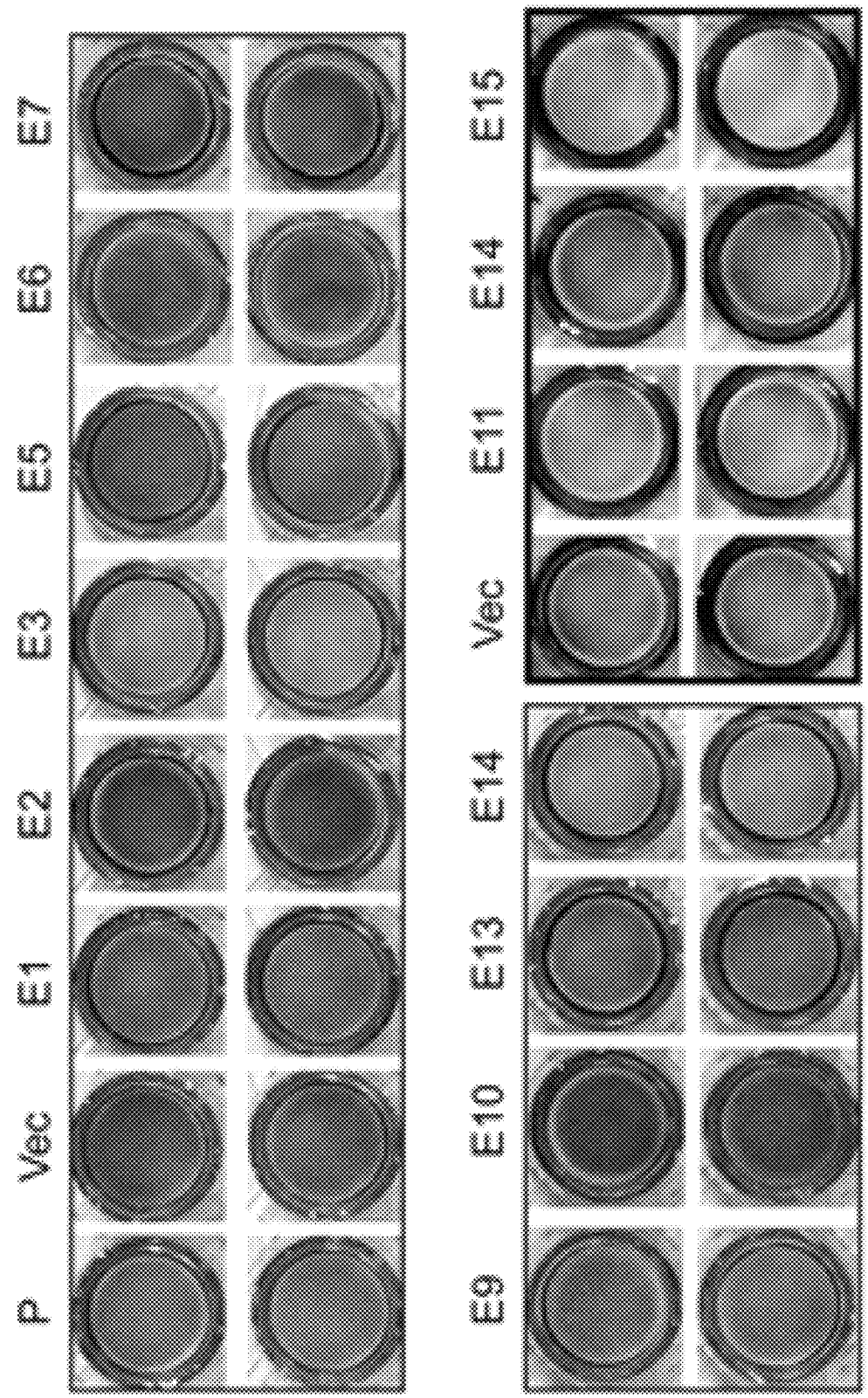
FIG. 4A is a photograph of the bottom surface of transwell inserts from the matrigel cell invasion assay described in Example 5, initiated with parental cultures of U251 cell lines stably transfected with the E1-E3, E5, E6-E7, E9-E10, E11, and E13-E15 pcDNA 3.1+ constructs described in FIG. 2 and Example 1; vector pcDNA 3.1+(Vec); and U251 parental control cells (P).

FIG. 4A is a photograph of cell plates from the MATRIGEL® cell invasion assay described in Example 5, initiated with parental cultures of U251 cell lines stably transfected with the E1, E2, E3, E5, E6, E7, E9, E10, E11, E13, E14, and E15 pcDNA 3.1+constructs described in FIG. 2 and Example 1 and with plasmid vector pcDNA 3.1+(Vec) and with U251 parental control cells (P). The results indicate that the EFEMP1 protein variants expressed from constructs E3, E11, and E15 suppress the invasiveness of U251 cells in the MATRIGEL® assay.

Figure 4B:
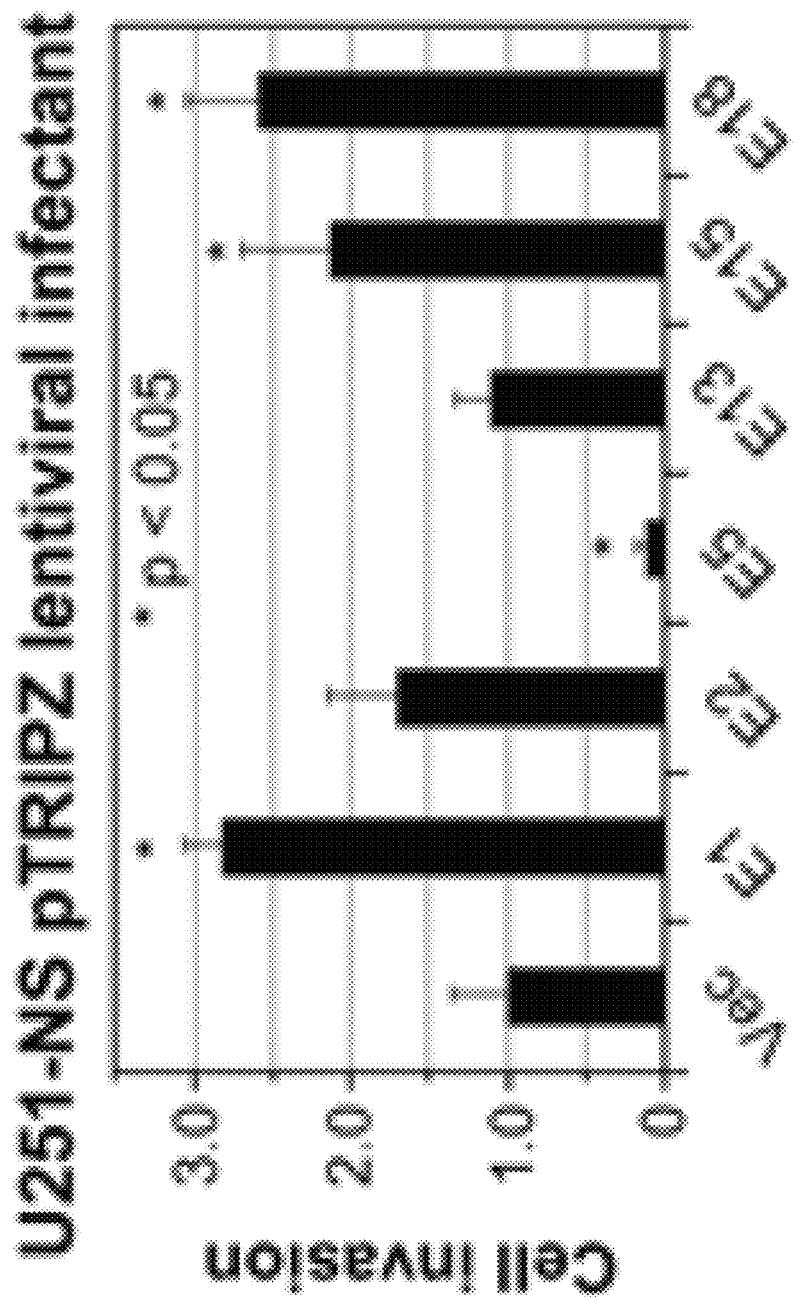
FIG. 4B is a plot of cell invasion from the matrigel invasion assay described in Example 5, initiated with neural sphere cultures of U251 cells infected with the E1, E2, E5, 13, E15, and E18 pTRIPZ lentiviral constructs described in FIG. 4A is a photograph of the bottom surface of transwell inserts from the MATRIGEL® (protein mixture) cell invasion assay described in Example 5, initiated with parental cultures of U251 cell lines stably transfected with the E1-E3, E5, E6-E7, E9-E10, E11, and E13-E15 pcDNA 3.1+constructs described in FIG. 2 and Example 1; vector pcDNA 3.1+(Vec); and U251 parental control cells (P).

FIG. 4B is a plot of cell invasion in the MATRIGEL® invasion assay described in Example 5, initiated with neural sphere cultures of U251 (U251-NS) cells infected with the E1, E2, E5, E13, E15, and E18 pTRIPZ lentiviral constructs described in FIG. 2 and Example 2 and with plasmid vector pTRIPZ (Vec). Lentiviral infectants were cultured in medium containing doxycycline to induce transgene expression, and expression was verified by assaying RFP expression with a fluorescent microscope. The results indicate that the EFEMP1 protein variant expressed from construct E5 significantly inhibits U251-NS cell invasion; whereas the wild-type EFEMP1 and EFEMP1 protein variants expressed from constructs E1, E15, and E18 significantly promote U251-NS cell invasion.

Figure 4C:
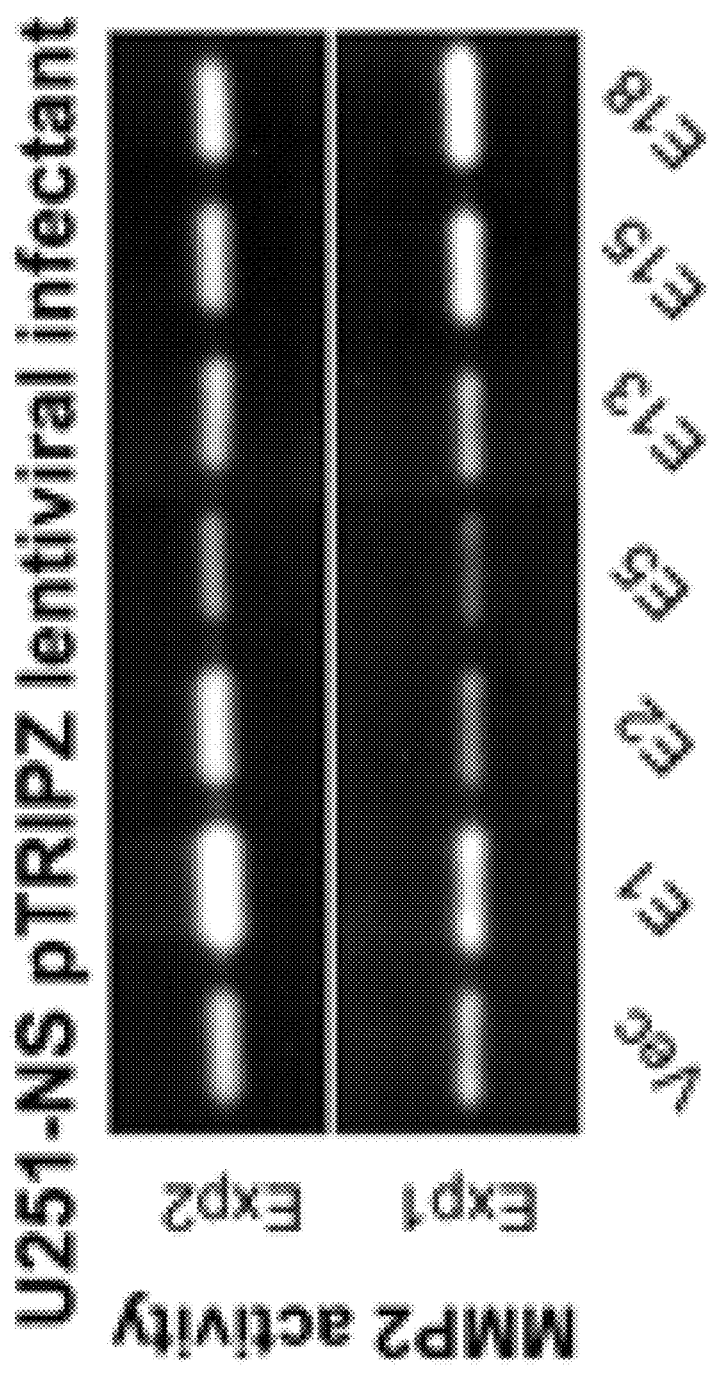
FIG. 4C is a photograph of gels of the zymography assay described in Example 6, conducted with cells of the MATRIGEL® invasion assays pictured in FIG. 4B.

FIG. 4C is a photograph of two gels of the zymography assay described in Example 6, conducted with cells from the MATRIGEL® invasion assay pictured in FIG. 4B. The results indicate that U251-NS glioma cells secrete active MMP2 (~67 kD), detected by the zymography assay. MMP2 is a protease highly expressed by glioma cells and is responsible for cell invasion. Also that the EFEMP1 protein variant expressed from construct E5 significantly inhibits U251-NS glioma cell production of activated MMP2; whereas the wild-type EFEMP1 and EFEMP1 protein variants expressed from constructs E1, E15, and E18 significantly promotes U251-NS glioma cell production of activated MMP2.

Figure 5:
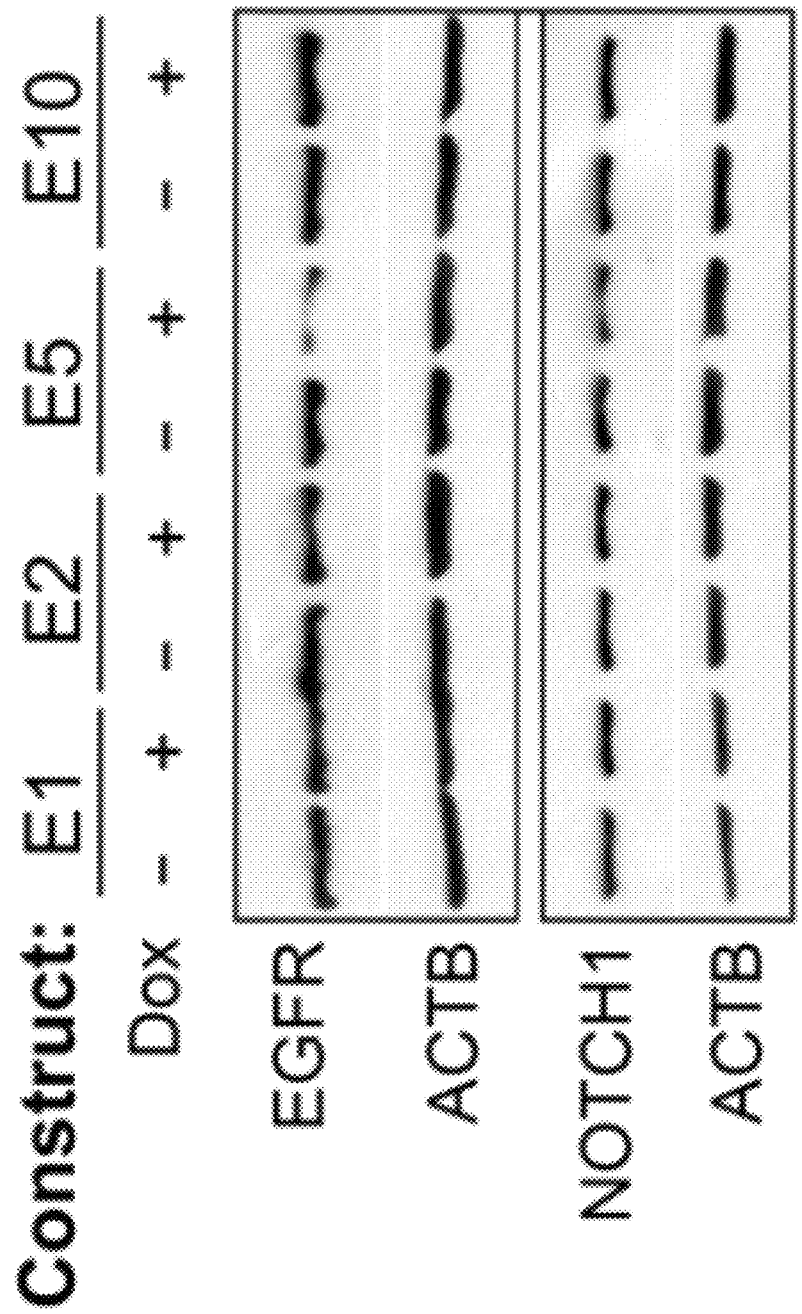
FIG. 5 is a photograph of immunoblots described in Example 7, conducted with parental culture U251 cells infected with the E1, E2, E5, and E10 pTRIPZ lentiviral constructs described in FIG. 2 and Example 1.

FIG. 5 is a photograph of immunoblots described in Example 7, conducted with parental culture U251 cells infected with the E1, E2, E5, and E10 pTRIPZ lentiviral constructs described in FIG. 2 and Example 1. Lentiviral infectants were cultured in medium containing doxycycline to induce transgene expression for 3 days, and expression was verified by assaying RFP expression with a fluorescent microscope. About 40% of gliomas overexpress EGFR, and EGFR activation is functionally related to enhanced cell survival and growth. Activation of Notch signaling by increasing NOTCH1 expression is a common feature of cancer stem cells. The results indicate that the EFEMP1 protein variant expressed from the E5 construct reduces the expression of EGFR and NOCTH 1 at protein level in U251 cells. ACTB expression level was used to indicate equal protein loading.

Figure 6:
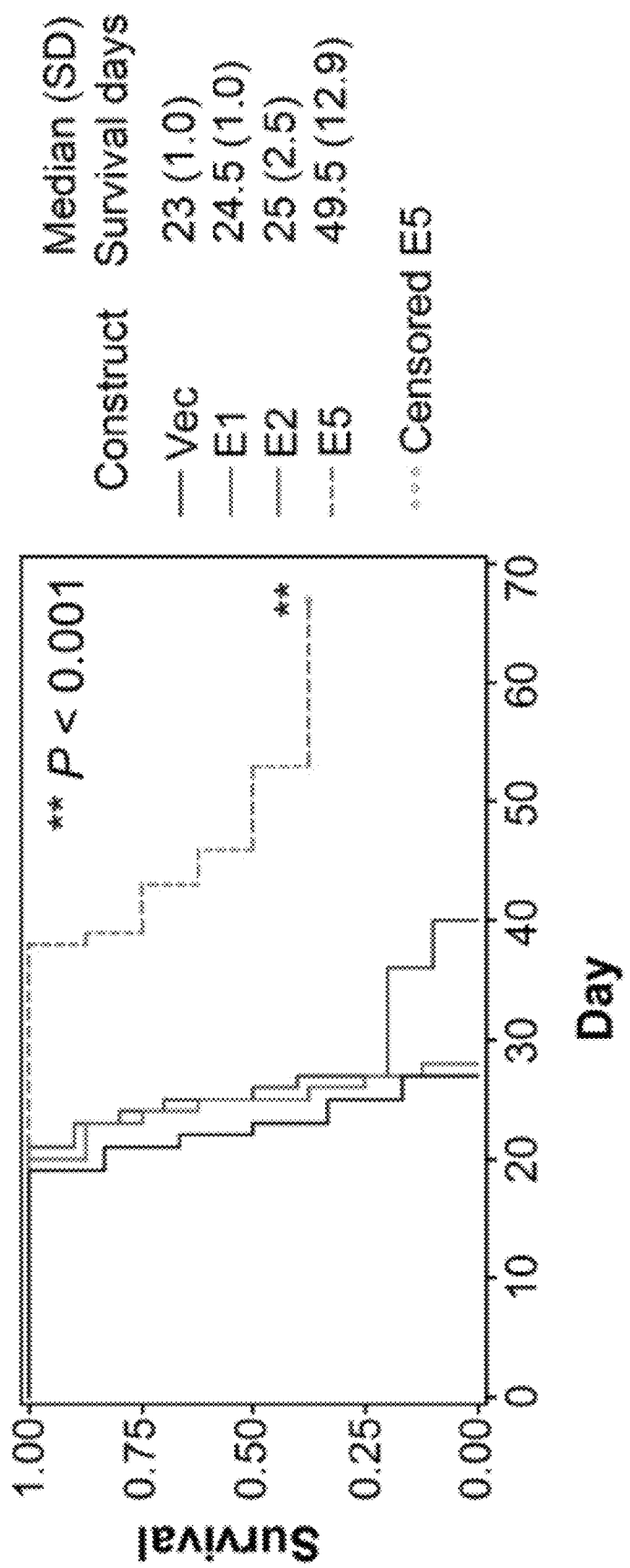
FIG. 6 is a survival plot for mice from the I.C. xenograft assay described in Example 8, initiated with neural sphere cultures of U251 cells infected with the E1, E2, and E5 pTRIPZ lentiviral constructs described in FIG. 2 and Example 1.

FIG. 6 is a Kaplan-Meier survival plot, carried out with mice from the intracranial xenograft assay described in Example 8, initiated with neural sphere cultures of U251 (U251-NS) cells infected with the E1, E2, and E5 pTRIPZ lentiviral constructs described in FIG. 2 and Example 1. Mice were fed with doxycycline-containing water from day 1 and throughout the experiment. RFP-expression was shown in the resulting tumors. The results indicate that the EFEMP1 protein variant expressed from the E5 construct inhibits tumorigenecity of U251-NS cells, measured by significantly prolonged survival, with median survival time more than doubled.

Taken together, the data and results set forth above indicate that the E5 EFEMP1 protein variant is a potent ETSP. The amino acid sequence of the FLAG tagged E5 EFEMP1 protein variant is set forth in SEQ ID NO:1. The amino acid sequence of a non-FLAG tagged E5 EFEMP1 protein variant is set forth in SEQ ID NO:2.

The present invention provides compositions and methods for treating cancer. In one embodiment, the invention provides a composition comprising a therapeutic peptide. In certain instances, the therapeutic peptide is referred to herein as "ZR30". In one embodiment ZR30 is derived from EFEMP-1 derived tumor suppressor protein (ETSP), which has been shown to possess therapeutic effects with multiple tumor growth suppression mechanisms of action (MOA), including targeting EGFR/AKT-mediated cell growth, MMP2-mediated cell invasion and angiogenesis, and NOTCH-mediated cancer cell stemness. In one embodiment ZR30 is based on the sequence of ETSP, wherein the N-terminal signal peptide is excluded. In one embodiment, the invention provides a composition comprising a protein having an amino acid sequence of SEQ ID NO:14, or a fragment or variant thereof. In some embodiments, the invention provides a nucleic acid encoding a ZR30, ZR30 peptide fragment or a ZR30-derived peptide. In one embodiment, the present invention provides a composition comprising a nucleic acid molecule which encodes a protein comprising an amino acid sequence of SEQ ID NO:14, or a fragment or variant thereof. In another embodiment, the nucleic acid molecule comprises a nucleotide sequence of SEQ ID NO:23.

In one aspect, the invention provides methods for treating or preventing cancer in a subject. In one embodiment, the method comprises administering to the subject an effective amount of a composition comprising a protein comprising an amino acid sequence of SEQ ID NO:14, or a fragment or variant thereof. In one aspect, the invention provides methods for treating or preventing cancer in a subject by administering the composition to the extracellular matrix compartment of the cancer cell. In another embodiment, the method comprises administering to the subject an effective amount of a nucleic acid molecule comprising a nucleotide sequence encoding a peptide comprising SEQ ID NO:14. In another embodiment, the method comprises administering to the subject an effective amount of a nucleic acid molecule comprising a nucleotide sequence of SEQ ID NO:23.

Compositions of the Invention

In one aspect, the invention provides compositions comprising an EFEMP1 protein variant. In some embodiments, the composition comprises ZR30, ZR30 peptide fragment or a ZR30-derived peptide. For example, in some embodiments, ZR30, ZR30 peptide fragment or a ZR30-derived peptide comprises the amino acid sequence of SEQ ID NO:14, or a fragment or variant thereof. The compositions may be used, for example, to treat or prevent cancer. In one embodiment, the composition comprises a peptide that possesses at least one activity selected from the group consisting of an inhibition of cancer cell invasion, an inhibition of tumor growth, and an inhibition of cancer recurrence.

In certain embodiments, the composition comprises a peptide comprising an amino acid sequence that shares at least about 70%, about 75%, about 80%, about 85%, about 90%, about 95%, about 97%, about 99%, or 100% identity with an amino acid sequence set forth in SEQ ID NO:1, 2, 3, 4, 5, 6, 7, 8, 9, 10, 11, 12, 13, or 14.

As known in the art the "similarity" between two peptides is determined by comparing the amino acid sequence and its conserved amino acid substitutes of one polypeptide to a sequence of a second polypeptide. Variants are defined to include peptide sequences different from the original sequence, for example, different from the original sequence in less than 40% of residues per segment of interest, different from the original sequence in less than 25% of residues per segment of interest, different by less than 10% of residues per segment of interest, or different from the original protein sequence in just a few residues per segment of interest and at the same time sufficiently homologous to the original sequence to preserve the functionality of the original sequence. The degree of identity between two peptides is determined using computer algorithms and methods that are widely known for the persons skilled in the art. The identity between two amino acid sequences may be determined by using the BLASTP algorithm [BLAST® (sequence algorithm) Manual, Altschul, S., et al., NCBI NLM NIH Bethesda, Md. 20894, Altschul, S., et al., J. Mol. Biol. 215: 403-410 (1990)].

A peptide of the invention may be synthesized by conventional techniques. For example, the peptides may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). In addition to being synthesized by solid phase techniques (Roberge J Y et al (1995) Science 269: 202-204), a peptide of the invention can be cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The variants of the peptides according to the present invention may be (i) one in which one or more of the amino acid residues are substituted with a conserved or non-conserved amino acid residue (for example, a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of a peptide of the invention.

A peptide or protein of the invention may be phosphorylated using conventional methods such as the method described in Reedijk et al. (The EMBO Journal 11(4):1365, 1992).

Cyclic derivatives of the peptides of the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to compositions comprising a peptide of the invention fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue. A targeting domain may target the peptide of the invention to a cellular component. In one embodiment the targeting domain directs the peptide to a tumor cell. For example, in certain embodiments, the targeting domain may bind to, or otherwise associate with, a tumor-specific antigen or tumor-associated antigen.

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain the peptide fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

In one embodiment of the present invention, a therapeutic agent is fused or linked to the peptide. In some embodiments, the therapeutic agent is a therapeutic peptide. This fusion protein (or other compound) may be produced by construction of a fusion gene incorporating a nucleotide sequence encoding a peptide of the invention and a nucleotide sequence encoding the therapeutic protein, and introducing this new genetic fusion (fusion gene) into a protein expression system, expressing the fusion protein encoded by the fusion gene, and isolating the fused protein for use as a therapeutic drug. Alternatively, the fusion may be accomplished by direct chemical fusion or conjugation yielding fusion of a peptide of the invention with the therapeutic agent. In one embodiment, the fusion protein comprises a linker or spacer sequence of amino acids between the peptide and the therapeutic agent or compound. Examples of linker or spacer sequences are well known in the art.

The therapeutic agents contemplated within the scope of the invention include, but are not limited to large molecular weight molecules including therapeutic proteins and peptides, siRNA, antisense oligonucleotides, and oligosaccharides. Other therapeutic compounds and agents contemplated within the scope of the invention include small molecular weight drug compounds including but not limited to vitamins, co-factors, effector molecules, and inducers of health promoting reactions.

In one embodiment, the present invention provides a composition comprising an isolated nucleic acid molecule encoding a peptide of the invention (e.g., EFEMP1 protein variant, ZR30, or variant thereof) or a biologically functional fragment thereof.

In various embodiments, the isolated nucleic acid molecule encodes one or more peptides comprising one or more amino acid sequences of SEQ ID NO:1, 2, 3, 4, 5, 6, 7, 8, 9, 10, 11, 12, 13, and 14. In one embodiment, the nucleic acid molecule comprises a nucleotide sequence of SEQ ID NO:23.

In one embodiment, the composition comprises an isolated nucleic acid sequence encoding a biologically functional fragment of a peptide of the invention. As would be understood in the art, a biologically functional fragment is a portion or portions of a full length sequence that retain the biological function of the full length sequence. Thus, a biologically functional fragment of a peptide of the invention comprises a peptide that retains the function of the full length peptide. In various embodiments, the isolated nucleic acid sequence encodes a ZR30 peptide comprising the amino acid sequence of SEQ ID NO:14. In certain embodiments, the isolated nucleic acid sequence encodes a ZR30-derived peptide.

Further, the invention encompasses an isolated nucleic acid encoding a peptide having substantial homology to a peptide disclosed herein. In certain embodiments, the isolated nucleic acid sequence encodes a peptide having at least 75%, 80%, 85%, 90%, 95%, 96%, 97%, 98%, or 99% sequence homology with an amino acid sequence set forth in SEQ NO:1, 2, 3, 4, 5, 6, 7, 8, 9, 10, 11, 12, 13, or 14.

Further, the invention encompasses an isolated nucleic acid molecule comprising a nucleotide sequence having substantial homology to a nucleotide sequence disclosed herein. In certain embodiments, the isolated nucleic acid molecule comprises a nucleotide sequence having at least 75%, 80%, 85%, 90%, 95%, 96%, 97%, 98%, or 99% sequence homology with the nucleotide sequence set forth in SEQ NO: 23.

In certain embodiments, the isolated nucleic acid molecule comprises a nucleotide sequence having at least 75%, 80%, 85%, 90%, 95%, 96%, 97%, 98%, or 99% sequence homology with a nucleotide sequence encoding SEQ ID NO: 1, 2, 3, 4, 5, 6, 7, 8, 9, 10, 11, 12, 13, or 14.

The isolated nucleic acid sequence encoding a peptide disclosed herein can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding a peptide of the invention, or functional fragment thereof. In one embodiment, the composition comprises an isolated RNA molecule encoding a peptide of the invention, or a functional fragment thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, NH2, NHR, NR2 or ON, wherein R is C1-C6 alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example, as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, for example, different from that which occurs in the human body. While they are referred to as "modified RNAs" they will of course, because of the modification, include molecules that are not, strictly speaking, RNAs. Nucleoside surrogates are molecules in which the ribophosphate1 backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone. Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding a peptide is typically achieved by operably linking a nucleic acid encoding the peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). An exemplary method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the present invention provides a delivery vehicle comprising a peptide disclosed herein, or a nucleic acid molecule encoding a peptide disclosed herein. Exemplary delivery vehicles include, but are not limited to, microspheres, microparticles, nanoparticles, polymerosomes, liposomes, and micelles. For example, in certain embodiments, the delivery vehicle is loaded with a peptide, or a nucleic acid molecule encoding a peptide. In certain embodiments, the delivery vehicle provides for controlled release, delayed release, or continual release of its loaded cargo. In certain embodiments, the delivery vehicle comprises a targeting moiety that targets the delivery vehicle to a treatment site.

The present invention provides a scaffold or substrate composition comprising a peptide disclosed herein, a nucleic acid molecule encoding a peptide disclosed herein, a cell producing a peptide disclosed herein, or a combination thereof. For example, in one embodiment, a peptide, a nucleic acid molecule encoding a peptide, a cell producing a peptide, or a combination thereof is present within a scaffold. In another embodiment, a peptide, a cell producing a peptide, a nucleic acid molecule encoding a peptide, or a combination thereof is applied to the surface of a scaffold. The scaffold of the invention may be of any type known in the art. Non-limiting examples of such a scaffold includes a, hydrogel, electrospun scaffold, foam, mesh, sheet, patch, and sponge.

Pharmaceutical Composition

For administration of a peptide of the invention or variant thereof to a subject, the peptide, nucleic acid molecule encoding the peptide, or variant thereof can be suspended in any pharmaceutically acceptable carrier, for example, sterile water or buffered aqueous carriers, such as glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein. The pharmaceutical compositions comprising a peptide of the invention, or nucleic acid molecule encoding a peptide of the invention may be prepared, packaged, or sold in the form of a sterile injectable aqueous or oily suspension or solution. This suspension or solution may be formulated according to the known art, and may comprise, in addition to the peptide or nucleic acid molecule, additional ingredients such as dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Formulations of a pharmaceutical composition suitable for parenteral administration comprise a peptide or nucleic acid molecule of the invention combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. In one embodiment, the preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Exemplary antioxidants for some compounds are BHT, BHA, alpha-tocopherol and ascorbic acid in the range of about 0.01% to 0.3% or BHT in the range of 0.03% to 0.1% by total weight of the composition. For example, the chelating agent is present in an amount of from 0.01% to 0.5% by total weight of the composition. Particularly, chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are the particularly exemplary antioxidant and chelating agents, respectively, for some compounds, other suitable and equivalent antioxidants and chelating agents may be substituted therefore as would be known to those skilled in the art.

Liquid suspensions may be prepared using conventional methods to achieve suspension of a peptide or nucleic acid molecule of the invention in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known thickening agents for oily suspensions include, for example, beeswax, hard paraffin, and cetyl alcohol.

A pharmaceutical composition used in the methods of the invention may be prepared, packaged, or sold in bulk, as a single unit dose, or as a plurality of single unit doses. As used herein, a "unit dose" is a discrete amount of the pharmaceutical composition comprising a predetermined amount of a peptide or nucleic acid molecule of the invention. The amount of the peptide or nucleic acid molecule is generally equal to the dosage of peptide or nucleic acid molecule which would be administered to a subject or a convenient fraction of such a dosage such as, for example, one-half or one-third of such a dosage.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Methods of the Invention

In one aspect, the invention provides a method for treating or preventing cancer. For example, in certain embodiments, the method inhibits cancer cell growth, cancer cell invasion and cancer recurrence. In one embodiment, the cancer cell is selected from the group consisting of high EGFR-expressing cancer cell or non-stem-like tumor mass-forming cell and high NOTCH-expressing cancer cell or stem-like tumor initiating cell.

In one aspect, the method results in modulating, in cancer cells, the activity and/or expression level of proteins that include EGFR, AKT, protein tyrosine kinase 2 (PTK2), and NOTCH. The cancer can be a low grade glioma, a medium grade glioma, a high grade glioma, such as GBM, a fibrosarcoma, a colorectal cancer, a lung cancer, a colon cancer, a liver cancer, a breast cancer, a prostate cancer, a pancreatic cancer, a skin cancer, a cervical cancer, a kidney cancer, a gastric cancer, or a nasopharyngeal cancer. In one aspect, the method suppresses the extracellular activity of MMP2 from cancer cells including but not limited to glioma, fibrosarcoma, colorectal, lung, colon, liver, breast, prostate, a pancreatic cancer, a skin cancer, a cervical cancer, a kidney cancer, a gastric cancer, or nasopharyngeal.

The methods of treatment of the invention include various administration methods, such as for example parenteral administration. As used herein, "parenteral administration" of a composition of the invention includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, bolus injections, and kidney dialytic infusion techniques. In one embodiment, parenteral administration includes intra-tumoral injection of a composition described herein into a tumor of a subject. In one embodiment, a therapeutically effective amount of the composition is administered to a subject by intra-tumoral injection.

The composition may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

In certain embodiments of the present invention, the composition is administered to a patient in conjunction with (e.g., before, simultaneously or following) any number of relevant treatment modalities, including but not limited to treatment with radiation, chemotherapy, surgery, or any other known cancer treatment.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the exemplary embodiments of the present invention, and are not to be construed as limiting in any way the remainder of the disclosure.

Example 1: EFEMP1 Deletion/Mutation Constructs

Expression constructs encoding the E1, E2, E3, E4, E5, E6, E7, E8, E9, E10, E11, E13, E15, and E18 wild-type and variant EFEMP1 proteins illustrated in FIG. 2 and described above were made by PCR, with primers designed to create restriction sites for cloning and/or ligation of two separate cDNA fragments of EFEMP1. PCR products were cloned into TA-cloning vector pCR4.0 and sequence verified, prior to subcloning into mammalian expression vector pcDNA3.1+(Life Technologies) and lentiviral vector pTRIPZ. A shuttle vector had been made to introduce internal ribosome entry site for expression of EFEMP1 wild-type and variant proteins in pTRIPZ (Thermo Scientific) under the same promoter for red fluorescent protein (RFP).

Example 2: U251 Lentiviral Infectants

U251 (parental and neural sphere cultures) lentiviral infectants were established by generating lentivirus from co-transfecting HEK293 with plasmid DNA constructs (lentiviral vector pTRIPZ-empty vector or pTRIPZ-EFEMP1 construct E1, E2, E3, E4, E5, E6, E7, E8, E9, E10, E11, E13, E15, and E18 together with its derived constructs, psAX2, and pCMV-VSV-G). The U251 lentiviral infectants were established after elimination of uninfected cells by a 1-2 week culture under selecting antibiotic (1.25 µg/ml puromycin) and addition of doxycycline (1 µg/ml) to monitor success of infection via RFP expression in live cells with inverted fluorescent microscopy.

U251 stable transfectants. U251 stable transfectants were established by transfecting with with plasmid DNA constructs (pcDNA3.1 vector or pcDNA-E1, E2, E3, E4, E5, E6, E7, E8, E9, E10, E11, E13, and E15), and cultured under selecting antibiotic (400 µg/ml neomycin) to form colonies. Individual colonies were picked using pipet tips, and transferred to 6-well plates to expand the colonies.

Example 3: Soft Agar Colony Formation Assay 800-1000 cells were mixed with 1 ml of 0.3% soft agar in DMEM/F12 supplemented with 5% bovine serum or a mitogen supplement for NS cultures described in Example 10, spread onto hardened 0.5% soft agar in the same medium (1 ml per well in four corner wells of a 6-well plate). 1 ml of the same medium was added 2 and 3 weeks later and colony numbers were counted 4 weeks later under a microscope with a 4× lens. The cells were U251 control cells and U251 cells stably transfected with constructs E1, E2, E3, E4, E5, E6, E7, E8, E9, E10, E11, E13, E14, E15, or pcDNA-empty vector (Vec). The cells were cultured in medium containing doxycycline to induce transgene expression. Total number of colonies in each well were counted under microscope with 4× lens and normalized to average number of colony from Vec control (set in uninity). The average (Ave) and standard deviation (SD) were based on colonies formed 4 individual wells. 5-10 Representative colonies were measured and scaled by the diameter of the colony: 1+(~10 µm), 2+(~20 µm), 3+(30-40 µm), 4+(40-60 µm), 5+(50-100 µm), 6+(100-200 µm).

Example 4: Subcutaneous (S.C.) Xenograft Assay

Parental cultures of U251HF lentiviral infectant cell lines pTRIPZ-vec and pTRIPZ-E1, E2, E5, E11, E13, E15, and E18 were grown in media containing 1 µg/ml doxycycline. $2.5 \times 10^6$ U251HF lentiviral infectant cells in 50 µl DMEM/F12 containing 14×diluted MATRIGEL® (original concentration 9-12 mg/ml) were subcutaneously injected into female nude mice (strain NCrNu-M, Taconic, Hudson, N.Y.) that were 4-6 weeks old, anterior to their right and left thighs on both sides. Injected mice were provided with water containing 1 µg/ml doxycycline the day of injection. Tumors were removed 25 days after injection, weighed, and analyzed by t-test (paired, two tailed).

Example 5: MATRIGEL® Invasion Assay 9-12 mg/ml MATRIGEL® was thawed on ice or at 4° C. 10 ml ice cold serum free medium was added to the thawed MATRIGEL®. Plates were prepared by diluting thawed MATRIGEL® with ice cold SF-DMEM/F12, adding 200 µl to transwell (12 well; 8 µm), and then incubating at room temp for >1 hour. Before plating cells, unbound material was gently aspirated off. The MATRIGEL® coating was colorless and not visible. Cells were prepared by detaching cells grown in 100 mm dishes to 80-90% confluency, by washing with 10 ml PBS, digesting with 2 ml 0.05% trypsin-EDTA for 30 sec, removing the trypsin, detaching the cells by tapping the bottle, then adding 10 ml culture medium and pipetting up and down, and then transferring the cells to a 15-ml tube. The cells were then spun down, resuspended in 10-15 ml SF-medium, taking 10 µl to count cells with a hemocytometer. $5 \times 10^6$ cells were then spun down and resuspended in 5 ml SF-medium at $1 \times 10^6$/ml. $5 \times 10^5$ cells were added to coated transwell, and 1 ml 0.05% CS-medium was added to the to bottom well. Plating was done in a $CO_2$ incubator, where plates were then cultured for 24 hours.

Cells that penetrated the MATRIGEL® were stained with HEMA3 CMS as follows. 0.5 ml of fixative stain was added to the well of the plate and 0.2 ml was added to the transwell. The stain was removed after 20 minutes. Then, 0.5 ml of red stain was added to the well of the plate and 0.2 ml was added to the transwell. The stain was removed after 20 minutes. Then, 0.5 ml of dark blue stain was added to the well of the plate and 0.2 ml was added to the transwell. The stain was removed after 20 minutes. A Q-tip dipped in water was used to remove the MATRIGEL® membrane, which was then air dried. The dry membrane was placed on a slide and mounting medium was added. A coverslip was then placed on top, and 10 pictures were taken for each filter with a microscope using a 20× lens. Cells were then counted based on the pictures taken, compared to control (Vec), which was set to unity, and analyzed by t-test (paired, two tailed).

Example 6: Gelatin Zymography Assay

Conditioned medium of NS cultured U25F lentiviral infectant cells expressing wild-type EFEMP1 and variant EFEMP1 protein from constructs pTRIPZ-E1, E2, E5, E13, E15, or E18 cells, as well as NS culture U251HF control, pTRIPZ-vec cells, were grown for 48 hours in serum-free DMFM/F12 media containing 1 µg/ml doxycycline were collected as follows. Cells were spun down, and 0.3 ml supernatant was transferred into a 1.5 ml tube. Protein was precipitated from the supernatant by adding 1.2 ml cold acetone. The precipitate was spun immediately at 14K RPM for 5 min at 4° C. Condition medium protein (CM-P) was resuspended in 100 µl 1×RIPA+1× protease inhibitor cocktail. 2 µl of CM-P was taken to determine protein concentrate with a BIO-RAD Protein Assay. The resuspended CM-P was stored at 80° C.

2-4 µg of CM-P were mixed with, 1×RIPA, and 2× sample buffer (100 µl 10% BB, 10 ml glycerol, 1 g SDS, 7.5 ml 1 M Tris.HCl pH 6.8, add sterile ddH$_2$O to 50 ml), briefly spun, and loaded onto a zymography gel in 1×Tris-glycine-SDS running buffer. The gel was run at room temp @90 V for 2 hours. The gel was washed several times in 2.5% Triton X-100 for 1-2 hour at RT with gentle shaking. The gel was then incubated overnight at 37° C. in protease reaction buffer (50 mM Tris (pH=7.5), 10 mM CaCl2, 150 mM NaCl). The gel was then stained for 30 min with Coomassie Blue R-250 (0.1% coomassie blue, 10% acetic acid, 10% isopropanol in ddH$_2$O) with gentle shaking. The gel was then stained in 10% acetic acid, 30% methanol solution three times for 20 minutes, and air-dried overnight between two cellophane papers.

Example 7: Immunoblotting 30-40 µm protein of whole cell lysate were loaded onto 8% SDS-PAGE gel in 1×Tris-glycine-SDS running buffer. The gel was run at room temp, 90 V for 2 hours, and transferred to a nitrocellular membrane. The blots were blocked with 5% skim milk for 1 hour, then incubated in 1% BSA containing rabbit primary antibodies for EGFR (1:1000 dilution) or NOTCH1 (1:1000 dilution) overnight. Then blots were washed with 1×TB ST for 1 hour, incubated with anti-rabbit IgG HRP-conjugated secondary antibody (1:10, 000 dilution) for 1 hour. An ECL detection kit was used to develop the signal in the immunoblots.

Example 8: Intracranial (I.C.) Xenograft Assay

Glioma cells (1×105/3 µl DMEM/F12) were injected into the frontal lobe of 4-6 week old, female, nude mice (strain NCrNu-M, Taconic, Hudson, N.Y.), following IACUC approved surgical procedures. After I.C. implantation, mice were daily observed for moribund signs (hunchback posture, marked weight loss, and gait impairment) and periodically weighed. Mice were euthanized when they developed brain-damage symptoms (ataxia, hemiparesia, etc) and/or 20% body weight loss, and the following day was recorded as the survival date for survival analysis.

Example 9: Parental Culture of U251

U251 cells were cultured in regular tissue-culture-treated dishes, in DMEM/F12 medium supplemented with 5% bovine serum and 1× penicillin-streptomycin, at 37° C. with 5% $CO_2$, in a humidity chamber.

Example 10: NS Culture of U251

U251 cells were cultured in an agar (1%)-coated dish, with DMEM/F12 medium supplemented with 20 ng/ml EGF, 20 ng/ml bFGF, 0.3% B27, and 1× penicillin-streptomycin, at 37° C. with 5% $CO_2$, in a humidity chamber.

Example 11: An Engineered Synthesized Protein ZR30 Expresses its Anti-Cancer Effect in the Extracellular Compartment of Different Human Cancer Cell Lines and Glioma Cell Subpopulations in Intracranial Xenograft Models Human Glioma Cell Lines and Culture Conditions The human U251 and U87 cell lines were purchased from the Cell Bank Type Culture Collection of the Chinese Academy of Sciences (CBTC-CCAS, Shanghai, China). The genetic profile (7-STR markers) of the U251 matched the U-251 MG from the source of JCRB (See Table S2 in Hu et al. 2013). The human cell lines of LN229, T98G, Hela, WPMY-1 and PC-3 were originally purchased from ATCC. The human U251-GFP and U251NS-RFP cells were generated in the Brain Tumor Research Laboratory, University of California, Irvine. The U251-GFP line is the U251 line transduced with lentiviral vector of pGIPZ-Empty, which constitutively expresses green fluorescence protein (GFP) under CMV promoter. The U251NS-RFP line is the clonal line of U251-NS (U251-NS1) transduced with lentiviral vector of pTRIPZ-Empty, which expresses red fluorescence protein (RFP) under a doxycycline-inducible promoter. Authentication of U251 and U251NS and characterization of the molecular and tumorigenic phenotypes of U251-GFP and U251NS-RFP were shown in Hu et al., 2013, PLoS One, 8(11): e80898.

Cells were cultured in DMEM/F12 (all GBM cells, except U251NS), DMEM (Hela, WPMY-1), or RPMI-1640 (PC-3), supplemented with 5-10% fetal bovine serum. U251NS-RFP cells were cultured in DMEM/F12 supplemented with epidermal growth factor (EGF, 20 ng/ml), basic fibroblast growth factor (FGF, 10 ng/ml), and 1% B27 (Invitrogen, Carlsbad, Calif.). In experiments to examine the ZR30 effect on in vitro cultures, monolayer cultures of U251NS-RFP were achieved by culture in fibronectin (1 µg/cm$^2$)-coated dishes.

In Vitro Production and Purification of ZR30

A DNA fragment (named ZR30) was PCR-amplified from plasmid DNA containing the engineered DNA of ETSP (PCT/US14/32597), with two primers for removal of the N-terminal part having the FLAG and signal peptide. PCR amplified ZR30 was cloned to the Xho I and Not I site of the pEG vector, and GST-ZR30 protein was synthesized using a wheat germ cell free system, purified by Glutathione Sepharose 4 Fast Flow, then PreScission™ Protease was used to remove GST tag to produce ZR30 in PBS solution (Abnova, Taiwan).

Gelatin Zymography and Immunoblotting

For the gelatin zymography assay, overnight cultures of U87 and U251 at 40-50% cell confluences were washed with PBS, and returned to culture for 2-3 days in serum-free (SF) DMEM/F12 media with or without adding a few µL of ZR30 (140 ng/µL in PBS), to reach various concentrations (e.g. 10, 50, 100 ng/ml). Conditioned media were collected after removing cells by a brief centrifugation, and the proteins were precipitated using 4 volumes of cold acetone and centrifugation 14,000 rpm for 5 minutes, and then resuspended in radioimmunoprecipitation assay buffer (RIPA) containing Protease Inhibitor Cocktail (Roche) for the Gelatin zymography assay, following the method described previously (Mayes et al., 2006, Cancer Res, 66(20): 9809-9817).

For the immunoblotting assay, monolayer cultures of U251 and U251-NS in 15-20% cell confluence were cultured for 2-4 days in culture media (serum supplement for U251, growth factor supplement for U251-NS) with or without adding ZR30. For U251, a 2-day culture in serum-free media continued, with or without adding EGF 30 minutes prior to harvesting cells to obtain whole cell lysates. Proteins of whole cell lysates (30-40 µg) were used in immunoblotting for determining protein expressions of NOTCH1, EGFR and pAKT (Ser473). Primary antibodies (rabbit, 1:1000 dilutions) from Cell Signaling (Danvers, Mass.) were hybridized at 4° C. O/N, and the blots were washed with 1×TBST for 1 hour, incubated with IgG horseradish peroxidase (HRP)-conjugated secondary antibody (1:10,000 dilutions) for 1 hour. The blots were washed and re-probed with ACTB (IgM-specific mouse, 1:1000 dilutions) from Millipore (Temecula, Calif.), to control equal protein loading. A chemiluminescent detection of horseradish peroxidase (HRP) activity was used to show the signal in the immunoblots.

Intracranial (i.c.) Glioma Xenograft Models

BALB/c nude mice (SPF level, 6 weeks old) were purchased from the Shanghai Laboratory Animal Center (SLAC). Human glioma cell line U251, or a 1:1 ratio of U251-GFP and U251NS-RFP cells from transduction of U251 and U251-NS by lentiviral pGIPZ- or pTRIPZ-vector, respectively, were counted, resuspended to $1\times10^5$ cells in 3 µL DMEM/F12 for implantation into the right frontal lobes of nude mice. Mice were anesthetized by intraperitoneal injection of 1% sodium pentobarbital. After alcohol disinfection of the skin at the top of the head, a 0.5-1.0 cm longitudinal incision was made in the frontal area, 3.5 mm from the cerebral midline, 2 mm frontal to the coronal seam. Then the skull was carefully drilled with a needle tip. A 10-4, syringe containing 3 µL cells was vertically inserted through the skull, into the brain parenchyma 3 mm down from cerebral surface, and the cells were slowly injected over 2 min. Mice were observed daily after tumor cell implantation, to determine their tumor status, including neurological deficits and body weight loss. In the animal experiment with mice implanted with the cell mixture containing U251NS-RFP, mice were given autoclaved water containing doxycycline (1 mg/mL) throughout the experiment, in order to induce RFP expression by U251NS-RFP cells.

Intra-Tumoral (i.t.) Drug Administration

Following i.c. human glioma cell implantation, nude mice were randomized based on body weight into control and treatment groups (10 or 19-20 mice per group in two independent experiments) to receive intra-tumoral injection of PBS (control) or ZR30 (treatment) at the same volume. The i.t. injection was performed after the mice were anesthetized and frontal lobe skin was cut to expose the site of tumor cell injection. A 10-µL syringe containing 5-10 µL PBS or ZR30 was inserted vertically through the cell injection site to a depth of 3.5 mm from cerebral surface, and then the solution was slowly injected into the tumor-forming site over 2 minutes.

Animal Survival Analysis

Survival times were recorded for mice that were sacrificed when they showed moribund signs (hunchback posture and/or 20% weight loss) and the following day was recorded as the survival date. For mice found dead, the previous day was recorded as the survival date. Overall survival of mice bearing intracranial glioma xenografts was estimated using Kaplan-Meier survival curves, and P values were determined from Log-Rank statistics on pair-wise comparisons of the two groups using Cox Regression. The significance level was set at $P<0.01$ in order to adjust for the multiple comparisons without overinflating Type II error. SAS versions 9.2 and 9.3 (The SAS Institute, Cary, N.C.) were used for all analyses.

Comparative Quantitative Polymerase Chain Reaction (CQ-PCR) on DNA Samples of Nude Mouse Brains that Developed Human Gliomas from i.c. Tumor Cell Implantation Upon sacrifice, the entire right hemispheres of the mice were removed and the DNA was extracted using a genomic DNA extraction kit (Zymo Research, Irvine, Calif.). DNA was diluted with 10 mM Tris-HCl (pH7.5) and about 10-20 ng DNA in 4 µL was taken to quantify copy number of human gene (SPAG16) and mouse gene (Spag16) using a StepOne real-time PCR instrument (Applied Biosystems, Foster City), with PCR primer mix (10×) and four 10-fold serial diluted CQ-PCR standard (CQ112, $1\times10^5$, $1\times10^4$, $1\times10^3$, $1\times10^2$ per 4 µL) for quantifying human gene (SPAG16) and mouse gene (Spag16) (provided by Ziren Rsearch LLC, Irvine, Calif.) to set up a 10-µL reaction with 2 µL 5× FastStart DNA MasterPLUS SYBR® (nucleic acid stain) Green I (Roche, Indianapolis). Real-time CQ-PCR was similarly set up to quantify copy numbers of RFP and GFP in glioma cells transduced with pGIPZ- and pTRIPZ-lentiviral DNA, using CQ-PCR standard CQ107 for quantifying GFP and RFP. Primer sequences for CQ-PCR are 5'-GCAAGTGGCAATGGTGTTATC-3' (SEQ ID NO:15) and 5'-GCTGGCACATTTAACCAGTTC-3' (SEQ ID NO:16) for human SPAG16; 5'-AGCCATCTT-CAACAGAGTCC-3' (SEQ ID NO:17) and 5'-CTCTCTTGTGCTAATGGAGC-3' (SEQ ID NO:18) for mouse Spag16; 5'-ATGGAGAGCGACGAGAGC-3' (SEQ ID NO:19) and 5'-CGCCTTTGGTGCTCTTCATC-3' (SEQ ID NO:20) for GFP in pGIPZ-Vector, and 5'-AGGAGAA-CATGCACATGAAGC-3' (SEQ ID NO:21) and 5'-GCCGTACATGAAGCTGGTAG-3' (SEQ ID NO:22) for RFP in pTRIPZ.

Results

ZR30, a Synthetic Protein Based on ETSP, Made in a Cell-Free System

Figure 7B:
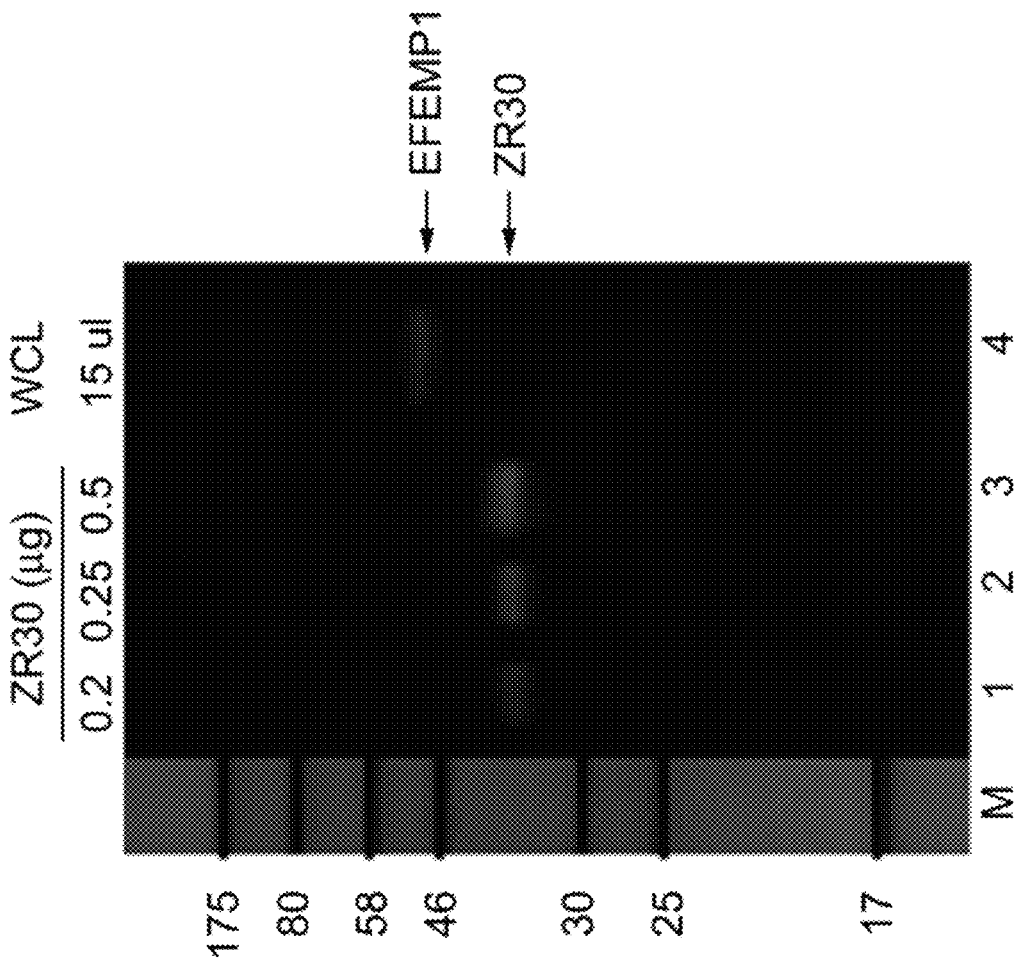
FIG. 7A and FIG. 7B are a set of images depicting the results of experiments detecting protein ZR30, based on the sequence of ETSP, which does not include the 81-bp region encoding the signal peptide used to transport the protein from the intracellular compartment into the extracellular compartment, made in a cell-free system.
Figure 7A:
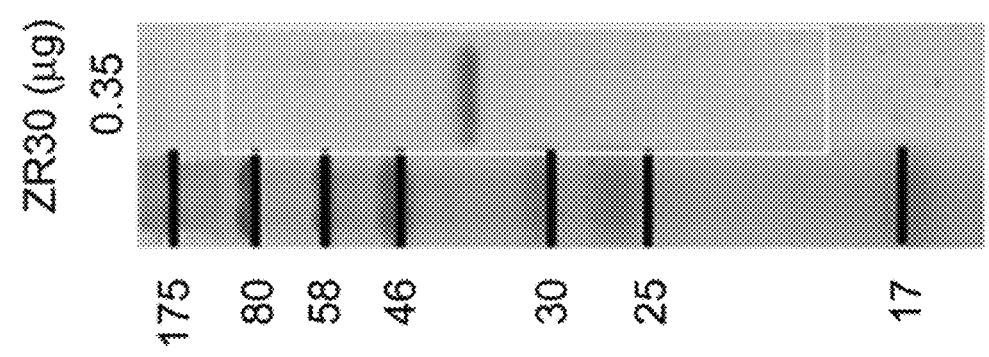

It has been demonstrated that EFEMP1 exerts its tumor suppression action within the tumor extracellular compartment (Hu et al., 2011, Mol Cancer, 10: 123). All the engineered EFEMP1 variants (including the one identified as ETSP) carry the signal peptides for extracellular transportation (Zhou et al. 2016, Oncoscience, DOI: 10.18632/oncoscience.306). Therefore, a protein made based on ETSP but excluding the signal peptide, when placed into the extracellular compartment of tumor cells, will have the same functions as ETSP synthesized via plasmid/lentivial vectors by transfected/transduced tumor cells. The signal peptide is responsible for exporting the protein from the intracellular compartment to the extracellular compartment. The signal peptide of EFEMP1 is in the region from the start codon to the $27^{th}$ amino acid, according to the exon/intron boundary and the homology among other fibulin members, hence the plasmid construct of ETSP was PCR amplified and subcloned into a plasmid DNA vector for in vitro protein production using a wheat germ cell-free system. The in vitro produced protein was purified using a GST-protein purification system. ZR30 is a 38.61 kDa protein following removal of GST (FIG. 7A), which is detectable by an antibody for human EFEMP1 (FIG. 7B).

ZR30 Suppresses Glioma Cells Making the Active Form of MMP2

It has been demonstrated that ETSP suppresses the extracellular active level of MMP2 made by glioma cells (Zhou et al. 2016, Oncoscience, in press). Using the same gelatin zymography assay, the effect of the in vitro synthesized ZR30 before or after removal of GST on MMP2 from two glioma cell lines, which expressed high (U87) and low (U251) levels of MMP2 was analyzed. As shown in FIG. 8A, the level of MMP2 in conditioned medium of U87 treated by ZR30 for 2 days was reduced to less than 40% the level of the untreated control. The suppressing effect of ZR30 on MMP2 was also shown in U251 (FIG. 8B). The ZR30-mediated inhibition of MMP2 activation was similarly observed in other human cell lines of GBM (LN229 and T98G), cervical cancer (Hela), prostate cancer stroma (WPMY-1) and metastatic prostate cancer (PC-3) (FIG. 8C).

ZR30 Targets EGFR, NOTCH, and ATK Signaling Pathways

Figure 9A:
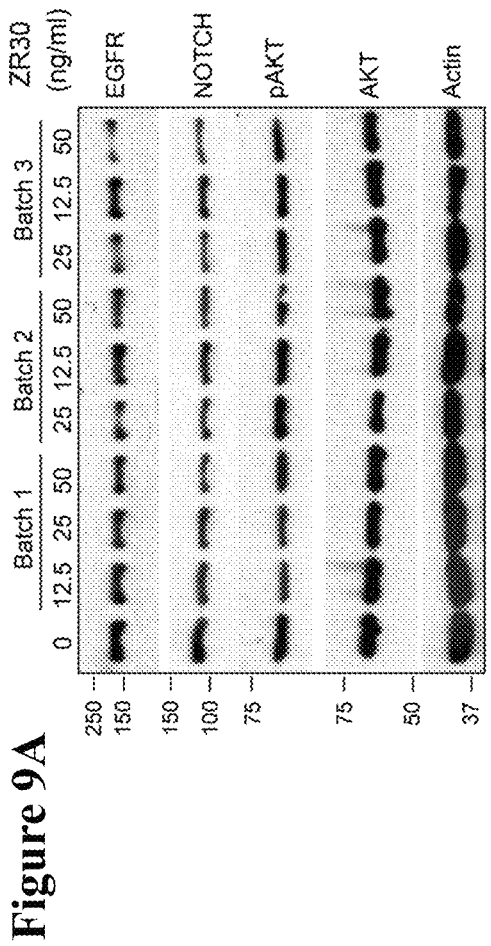
FIG. 9A through FIG. 9E are a set of images depicting the results of an Immunoblotting assay for detecting ZR30-treated glioma cells.
Figure 9B:
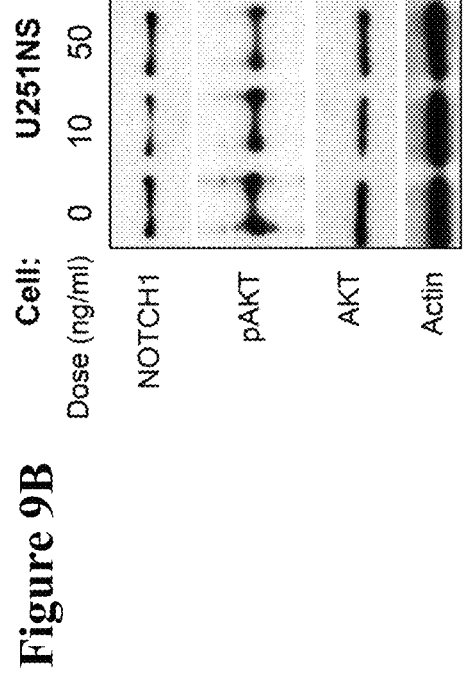

Further examination of the effect of ZR30 on EGFR and NOTCH1 proteins and downstream signals that were differentially activated in U251 and U251-NS and suppressed by overexpression of ETSP, was then carried out. The effect of ZR30 from three different production batches was examined using the same sets of U251 cells for a 4-day treatment at various dosages (12.5, 25, and 50 ng/ml). An immunoblotting assay was performed using whole cell lysates extracted from treated cells following a 2-day culture in basal (serum-free) medium. As shown in FIG. 9A, ZR30 of three production batches all showed strong suppression effects on NOTCH1, compared to untreated (0 ng/ml) control cells. ZR30 had an effect on the NOTCH and AKT signals in U251-NS cells (FIG. 9B), in which EGFR protein expression was barely detectable, but NOTCH1 expression was high (Hu et al., 2015, Oncotarget, 6(31): 30762-30772).

Figure 9D:
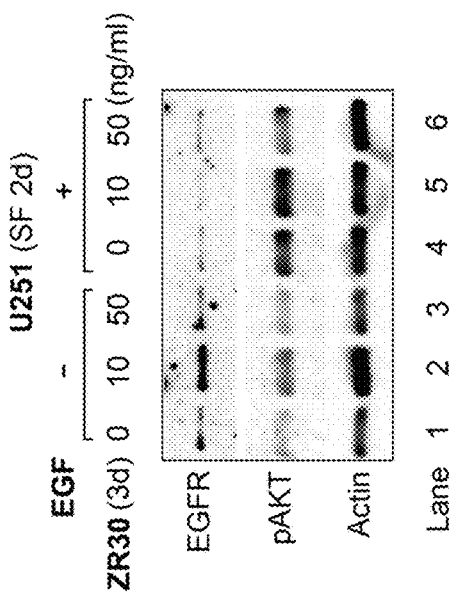
Figure 9C:
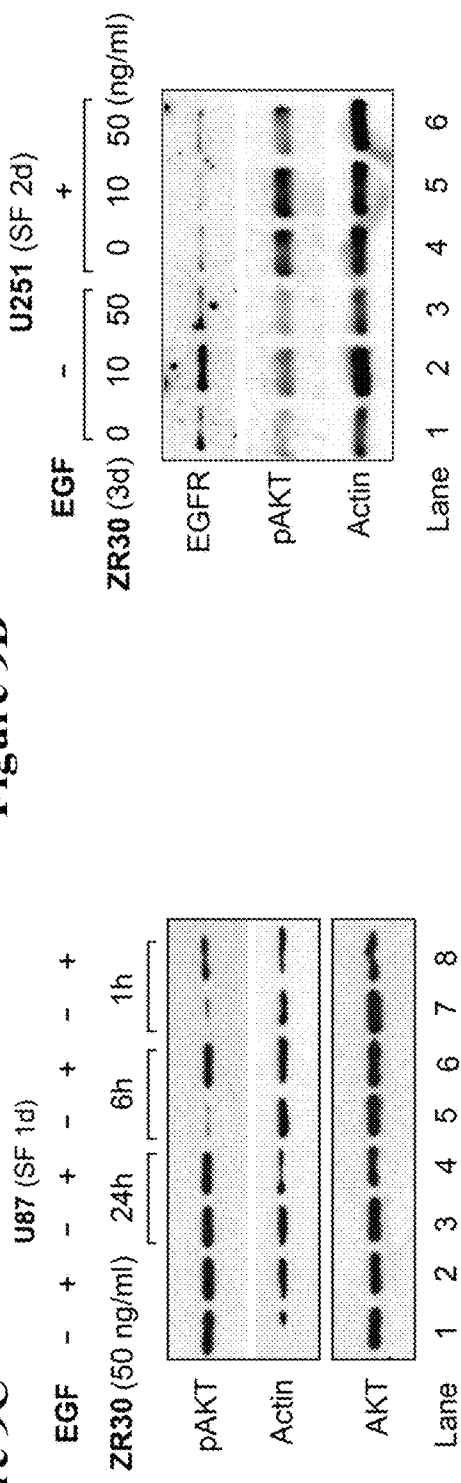
Figure 9E:
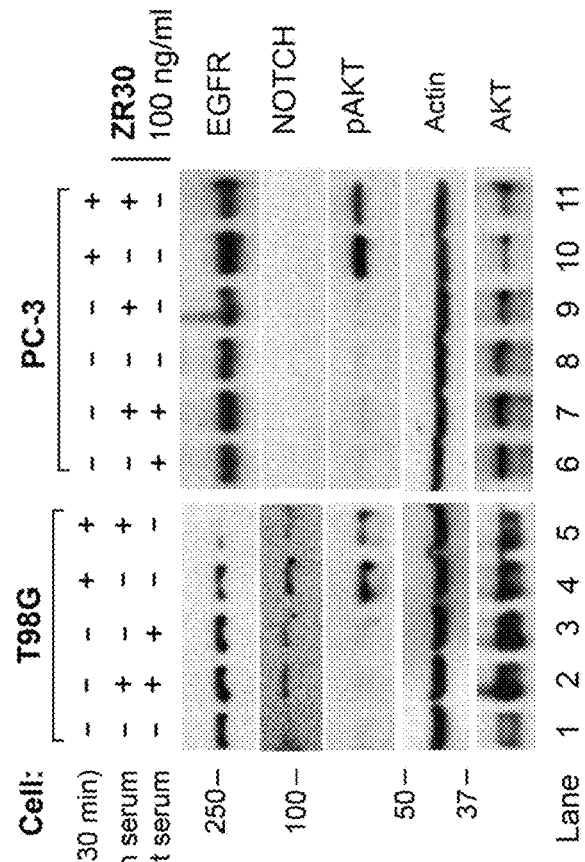

EFEMP1, the parental protein of ZR30, was shown to have the ability to compete with EGF on binding EGFR, and block EGF-activation by EGFR signaling in glioma cells, both by an in vitro GST-fusion protein of EFEMP1 (Hu et al., 2011, Mol Cancer, 10: 123) and transient overexpression of ectopic EFEMP1 by glioma cells (Hu et al., 2014, Oncoscience, 1(3): 205-15). ZR30 was shown to in GBM cell line U87 a short-term (1-6 h) effect in reducing the pAKT level (FIG. 9C, lanes 5 and 7), which was re-activated by EGF (FIG. 9C, lanes 6 and 8). Using the same experimental design, which was a 2-day serum-free culture following overexpression of EFEMP1 or addition of EFEMP1 or ZR30 to the culture medium, and then a 30-min exposure to EGF, it was demonstrated that ZR30 had the same effect in blocking EGF from activating EGFR, as was previously shown by EFEMP1. As shown in FIG. 9D (lanes 1 and 4), AKT phosphorylation was upregulated in response to a 30-min exposure to EGF along with a reduction of EGFR, which are indexes for EGF-mediated activation of EGFR signaling. As shown in FIG. 9C (lanes 4 and 6), ZR30 reduced cell response to EGF-stimulation. As shown in FIG. 9E, ZR30's capacity to disable the glioblastoma cells' ability to respond to EGF in activating EGFR/AKT signaling was also seen in another human cell line of GBM (T98G) and metastatic prostate cancer (PC-3) (lanes 5 and 11), compared to the control (lanes 4 and 10). Here an increase of NOTCH1 expression was observed (normalized to ACTB) in response to EGF in T98G, which was disabled by ZR30 (lanes 4 and 5). PC-3 does not express NOTCH1, hence no such effect was seen.

ZR30 Targets Both TMC and STIC Subpopulations in an Orthotopic Tumor Model

Data above showed reproducible protein production and consistent tumor suppressive effects of in vitro produced ETSP protein, ZR30, applied to the extracellular compartment of glioma-cell, in vitro cultures, by the same MOA as that of cells from overexpressing ETSP. To gain proof-of-concept data for the therapeutic effect of ZR30 in brain cancer, intra-tumoral (i.t.) injection of ZR30 into U251 intracranial (i.c.) xenografts in two independent animal experiments were performed.

One animal experiment started by i.c. co-implantation of defined mixtures (1:1 ratio, total$\times 10^5$ cells) of the syngeneic cell lines U251 and U251-NS transduced with lentiviral vectors for the expression of green (GFP) or red (RFP) fluorescent proteins, respectively. A week later, the same volume (10 µl) of ZR30 at three concentrations (18, 70, and 180 ng/µl) or PBS was i.t. injected through the hole and at the same depth as the cell implantation. According to information on animal weight loss, the time of treatment appeared to be at the stage of aggressive tumor development, and that ZR30 treatments at all doses did not appear to benefit survival. All animals in the control and treatment groups (13-16 mice/group) were euthanized 8-9 days following i.t. injection. The entire brains were removed, and the right hemispheres where tumor cells were implanted were cut out to extract DNA for CQ-PCR analysis, as described below.

Figure 10B:
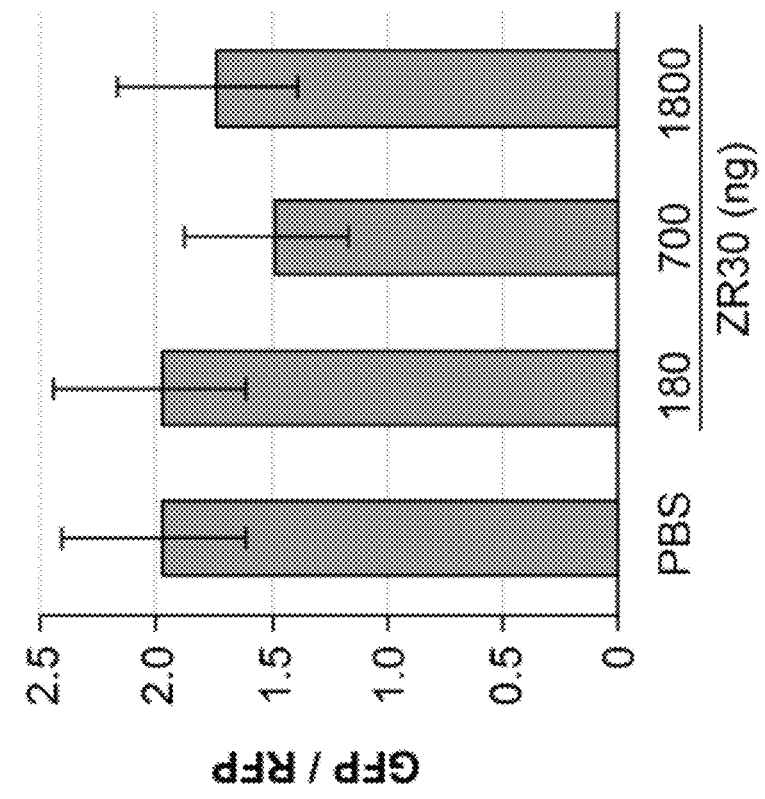
FIG. 10A and FIG. 10B are a set of images depicting the results of a comparative quantitative (CQ)-PCR assay illustrating the effect of ZR30 on glioma cell growth in an orthotopic model.
Figure 10A:
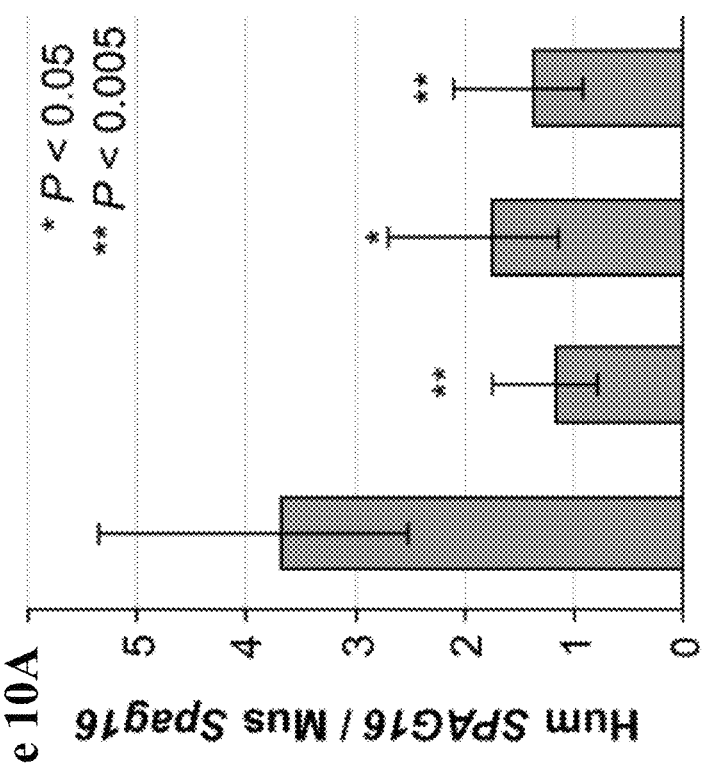

Comparative quantification of human and mouse genes by real-time PCR on DNA with human- or mouse-gene-specific primers on the single-copy gene SPAG16 in the human genome or Spag16 in the mouse genome was performed. As shown in FIG. 10A, an average 3.7 ratio of Hum SPAG16/Mus Spag16 DNA copies in PBS-treated mice indicated large volumes of human glioma xenografts grown in mouse right hemispheres. The ratios of Hum SPAG16/Mus Spag16 DNA copy were significantly reduced to average levels of 1.2, 1.7, and 1.4 in ZR30-treated mice at 180, 700, and 1800 ng dosages, respectively. The therapeutic effect of ZR30 in glioma was validated by data showing significant tumor suppression in the orthotopic glioma xenograft model from co-implantation of U251-GFP and U251NS-RFP cells.

Using CQ-PCR of GFP and RFP on the DNA samples of mouse brains from the control and treatment groups, ZR30 demonstrated to have an equal tumor-suppression effect on GFP-labeled U251 and RFP-labeled U251-NS, which differentially encompassed TMC and STIC, respectively, as characterized previously (Hu et al., 2013, PLoS One, 8(11): e80898). As shown in FIG. 10B, the ratio of GFP to RFP copy numbers in xenografts lacked a significant difference between control and ZR30-treated mice. Therefore, it had been concluded that, the tumor suppression effect from ZR30 applied equally to TMC and STIC subpopulations in orthotopic glioma xenograft model from co-implantation of U251-GFP and U251NS-RFP cells.

Validation of Therapeutic Efficacy of ZR30 by a Survival End-Point

To further prove ZR30's therapeutic potential for glioma treatment using the well-recognized survival end-point technique, an animal experiment was designed to determine survival improvement from ZR30 treatment using an orthotopic glioma xenograft model of U251 (U-251 MG from JCRB), which has relatively low i.c. tumorigenicity compared to that of the U251:U251NS mixed model. The latter contains an optimal ratio of TMC and STIC, which gave the highest i.c. tumorigenicity (Hu et al., 2013, PLoS One, 8(11): e80898). In this animal experiment, 36 mice were used that had similar weight and physical condition 1 week after i.c. tumor cell implantation, these mice were then divided into four groups (8-9 mice/group) to perform i.t. injection of 5 or 10 µl of PBS or ZR30 (70 ng/µl) at 10 or 21 days post i.c. cell implantation. Mice were followed to ethical end-points to record survival information, which was analyzed for statistical significance of the ZR30-treatment.

Figure 11A:
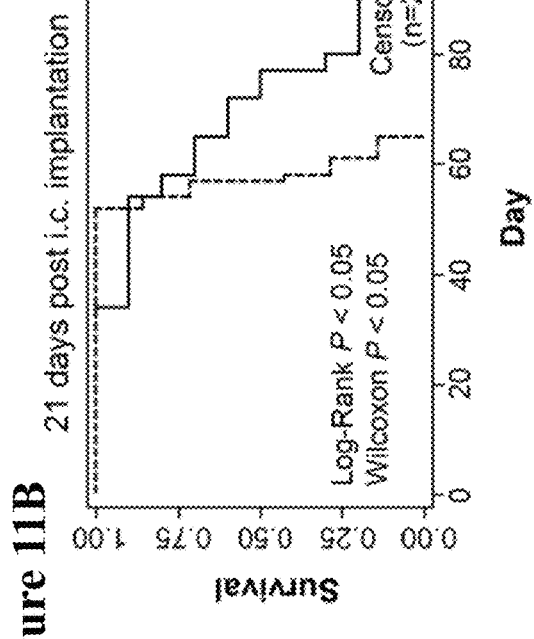
FIG. 11A and FIG. 11B are a set of images depicting the results of the Kaplan-Meier curves of mice in the orthotopic U251 glioma xenograft experiment with or without one-time i.t. injection of ZR30.
Figure 11B:
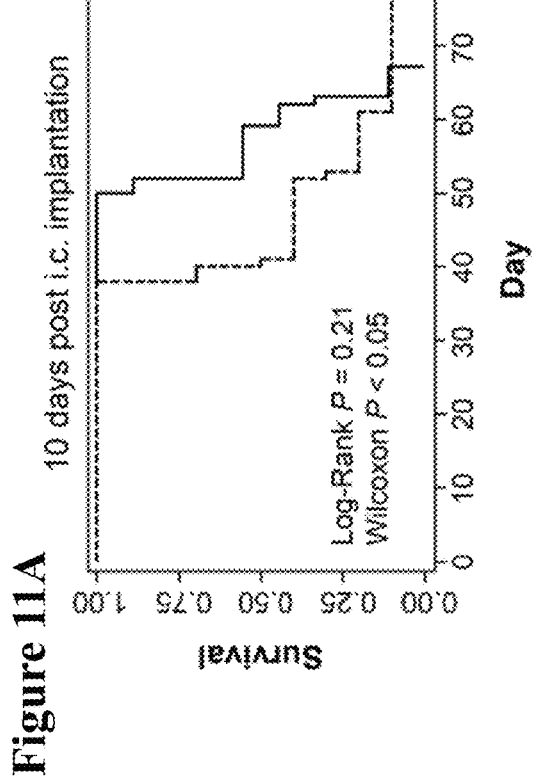

FIG. 11 shows Kaplan-Meier curves for survival of the control and treatment groups treated at 10 (FIG. 11A) and 21 (FIG. 11B) days post U251 cell implantation. Significantly longer survivals were observed for ZR30-treated mice compared to PBS-treated mice, for both treatment time points. Given the median animal survival time of 7-8 weeks in the control groups, the two treatment time points (10 and 21-days post cell implantation) appear to be at the stage of tumor onset and early tumor development, respectively. The observation that there is a survival benefit from ZR30 given at both of the time points is consistent with the tumor suppression effect of ZR30 in inhibiting both tumor onset and development. Furthermore, this is consistent with the identified MOA for ZR30, which targeted both the intracellular growth signaling pathways (EGFR, NOTCH, and AKT) for different tumor cell subpopulations and the MMP2-mediated pro-invasive, pro-angiogenic tumor microenvironments.

The Use of ZR30 for Treating Cancer

Effectively treating cancers, such as GBM, at an advanced stage has proven to be a difficult task. This is due to the ability of such cancers to evolve through tumor cell subpopulations that are under dynamic equilibrium through interplay with the tumor microenvironment. The discovery of ETSP was through models that show tumor heterogeneity as a fundamental cancer feature. The models used two syngeneic glioma cell lines, the parental cell line U251 and the clonal neural sphere line U251-NS, which predominantly contained high EGFR-expressing TMC and high NOTCH-expressing STIC subpopulations, respectively under two different culture conditions. It was found that the two cell types inter-converted by mis-segregation of chromosome 7 in response to environmental cues (Hu et al., 2013, PLoS One, 8(11): e80898). The functional analysis of an ETSP-based, in vitro-synthesized protein, ZR30, has also been carried out using these models of tumor heterogeneity, which is the only model so far with the power to show differentially two tumor cell subpopulations having behaviors relevant to the fast growing and high invasive natures of glioblastoma. Overall, the data showed the same tumor suppression effects of ZR30 on MMP2 production as reported by glioma cells expressing ETSP to inhibit cell invasion and angiogenesis. The effect of ZR30 on suppressing MMP2 activation was commonly observed in high-MMP2-expressing cells of brain, prostate and cervical cancers. The data also showed that ZR30 targets both TMC and STIC and blocks signaling transductions commonly activated in cancer cells, e.g. EGFR and/or NOTCH, and thus likely inhibits cell growth through blocking AKT-centered signaling pathways.

GBM is a deadly form of brain cancer, for which there is not yet any effective treatment despite 40 years of research/clinical trials. Although most GBMs were found to have overexpression of cell membrane receptor EGFR, pro-angiogenic protein VEGFA, and/or pro-invasive protein MMP2, there has been no success in improving survival with therapeutants targeting MMP2, EGFR and VEGFA alone nor in combination for the last two (Levin et al., 2006, J Neurooncol, 78(3): 295-302, Raizer et al., 2015, J Neurooncol, 126(1): 185-192). STIC in GBM are invasive tumor cells commonly found lacking the high expression of EGFR found in TMC subpopulations, but with high activation of NOTCH signaling to maintain "stemness". Currently, there is no report of success in treating GBM by targeting NOTCH signaling alone. ZR30's therapeutic effect, is demonstrated by suppressing both STIC and TMC together in orthotopic glioma xenografts by targeting MMP2, EGFR, NOTCH1, and ATK signaling from the extracellular compartment. Thus, the results presented herein point to a role for ZR30 in the inhibition of growth and invasive features of cancerous cells.

The following publications are hereby incorporated by reference in their entirety:

Lecka-Czernik B, Lumpkin C K Jr, Goldstein S. An overexpressed gene transcript in senescent and quiescent human fibroblasts encoding a novel protein in the epidermal growth factor-like repeat family stimulates DNA synthesis. Mol Cell Biol. 1995 January; 15(1):120-8.

Sun B S, Zhu X, Clayton M M, Pan J, Feitelson M A. Identification of a protein isolated from senescent human cells that binds to hepatitis B virus X antigen. Hepatology. 1998 January; 27(1):228-39.

Lissemore J L, Starmer W T. Phylogenetic analysis of vertebrate and invertebrate Delta/Serrate/LAG-2 (DSL) proteins. Mol Phylogenet Evol. 1999 March; 11(2):308-19.

Stone E M, Lotery A J, Munier F L, Neon E, Piguet B, Guymer R H, Vandenburgh K, Cousin P, Nishimura D, Swiderski R E, Silvestri G, Mackey D A, Hageman G S, Bird A C, Sheffield V C, Schorderet D F. A single EFEMP1 mutation associated with both Malattia Leventinese and Doyne honeycomb retinal dystrophy. Nat Genet. 1999 June; 22(2):199-202.

Marmorstein L Y, Munier F L, Arsenijevic Y, Schorderet D F, McLaughlin P J, Chung D, Traboulsi E, Marmorstein A D. Aberrant accumulation of EFEMP1 underlies drusen formation in Malattia Leventinese and age-related macular degeneration. Proc Natl Acad Sci USA. 2002 Oct. 1; 99(20):13067-72

Klenotic P A, Munier F L, Marmorstein L Y, Anand-Apte B. Tissue inhibitor of metalloproteinases-3 (TIMP-3) is a binding partner of epithelial growth factor-containing fibulin-like extracellular matrix protein 1 (EFEMP1). Implications for macular degenerations. J Biol Chem. 2004 Jul. 16; 279(29):30469-73.

Albig A R, Neil J R, Schiemann W P. Fibulins 3 and 5 antagonize tumor angiogenesis in vivo. Cancer Res. 2006 Mar. 1; 66(5):2621-9.

Fu L, Garland D, Yang Z, Shukla D, Raj endran A, Pearson E, Stone E M, Zhang K, Pierce E A. The R345W mutation in EFEMP1 is pathogenic and causes AMD-like deposits in mice. Hum Mol Genet. 2007 Oct. 15; 16(20):2411-22.

McLaughlin P J, Bakall B, Choi J, Liu Z, Sasaki T, Davis E C, Marmorstein A D, Marmorstein L Y. Lack of fibulin-3 causes early aging and herniation, but not macular degeneration in mice. Hum Mol Genet. 2007 Dec. 15; 16(24): 3059-70.

Yue W, Dacic S, Sun Q, Landreneau R, Guo M, Zhou W, Siegfried J M, Yu J, Zhang L. Frequent inactivation of RAMP2, EFEMP1 and Dutt1 in lung cancer by promoter hypermethylation. Clin Cancer Res. 2007 Aug. 1; 13(15 Pt 1):4336-44.

Invitrogen; pcDNA™3.1(+) pcDNA™3.1(−); Catalog nos. V790-20 and V795-20; Version K, 10 Nov. 2010 28-0104; User Manual.

Thermo Scientific Open Biosystems Expression Arrest TRIPZ™ Lentiviral shRNAmir; Technical Manual.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating cancer in a subject, comprising administering to the subject a therapeutically effective amount of a composition comprising an isolated polypeptide comprising an amino acid sequence selected from the group consisting of: a) SEQ ID NO:14; b) SEQ ID NO: 1; and c) SEQ ID NO: 2, wherein the cancer is a glioma.

2. The method of claim 1, wherein the method results in at least one activity selected from the group consisting of inhibition of cancer cell invasion, inhibition of cancer cell growth and inhibiting cancer cell recurrence.

3. The method of claim 1, wherein the tumor of the subject is characterized as-having activation of epidermal growth factor receptor (EGFR).

4. The method of claim 1, wherein the cancer is selected from the group consisting of a low grade glioma, a medium grade glioma, a high grade glioma, and human glioblastoma multiforme.

5. The method of claim 1, wherein the cancer is a glioblastoma multiforme.

6. The method of claim 1, wherein the therapeutically effective amount of the composition is administered to a subject by intra-tumoral injection.

7. The method of claim 1, wherein the tumor of the subject is characterized as having activation of NOTCH.

8. The method of claim 1, wherein the tumor of the subject is characterized as having activation of AKT.

9. The method of claim 1, wherein the tumor of the subject is characterized as having activation of an extracellular matrix metallopeptidase.

* * * * *

```
                       SEQUENCE LISTING

<160> NUMBER OF SEQ ID NOS: 23

<210> SEQ ID NO 1
<211> LENGTH: 386
<212> TYPE: PRT
<213> ORGANISM: Artificial sequence
<220> FEATURE:
<223> OTHER INFORMATION: Point mutated Homo sapiens

<400> SEQUENCE: 1

Met Asp Tyr Lys Asp Asp Asp Lys Leu Lys Ala Leu Phe Leu Thr
1               5                   10                  15

Met Leu Thr Leu Ala Leu Val Lys Ser Gln Asp Thr Glu Glu Thr Ile
                20                  25                  30

Thr Tyr Thr Gln Cys Thr Asp Gly Tyr Glu Trp Asp Pro Val Arg Gln
                35                  40                  45

Gln Cys Lys Asp Ile Asp Glu Cys Asp Ile Val Pro Asp Ala Cys Lys
        50                  55                  60

Gly Gly Met Lys Cys Val Asn His Tyr Gly Gly Tyr Leu Cys Leu Pro
65                  70                  75                  80

Lys Thr Ala Gln Ile Ile Val Asn Asn Glu Gln Pro Gln Gln Glu Thr
                85                  90                  95

Gln Pro Ala Glu Gly Thr Ser Gly Ala Thr Thr Gly Val Val Ala Ala
            100                 105                 110

Ser Ser Met Ala Thr Ser Gly Val Leu Pro Gly Gly Gly Phe Val Ala
            115                 120                 125

Ser Ala Ala Ala Val Ala Gly Pro Glu Met Gln Thr Gly Arg Asn Asn
        130                 135                 140

Phe Val Ile Arg Arg Asn Pro Ala Asp Pro Gln Arg Ile Pro Ser Asn
145                 150                 155                 160

Pro Ser His Arg Ile Gln Cys Ala Ala Gly Tyr Glu Gln Ser Glu His
                165                 170                 175

Asn Val Cys Gln Asp Ile Asp Glu Cys Thr Ala Gly Thr His Asn Cys
            180                 185                 190

Arg Ala Asp Gln Val Cys Ile Asn Leu Arg Gly Ser Phe Ala Cys Gln
        195                 200                 205

Cys Pro Pro Gly Tyr Gln Lys Arg Gly Asp Gln Cys Val Asp Ile Asp
    210                 215                 220

Glu Cys Thr Ile Pro Pro Tyr Cys His Gln Arg Cys Val Asn Thr Pro
225                 230                 235                 240

Gly Ser Phe Tyr Cys Gln Cys Ser Pro Gly Phe Gln Leu Ala Ala Asn
                245                 250                 255

Asn Tyr Thr Cys Val Asp Ile Asn Glu Cys Asp Ala Ser Asn Gln Cys
            260                 265                 270

Ala Gln Gln Cys Tyr Asn Ile Leu Gly Ser Phe Ile Cys Gln Cys Asn
        275                 280                 285

Gln Gly Tyr Glu Leu Ser Ser Asp Arg Leu Asn Cys Glu Asp Ile Asp
    290                 295                 300

Glu Cys Arg Thr Ser Ser Tyr Leu Cys Gln Tyr Gln Cys Val Asn Glu
305                 310                 315                 320
```

```
Pro Gly Lys Phe Ser Cys Met Cys Pro Gln Gly Tyr Gln Val Val Arg
                325                 330                 335

Ser Arg Thr Cys Gln Asp Ile Asn Glu Cys Glu Thr Thr Asn Glu Cys
                340                 345                 350

Arg Glu Asp Glu Met Cys Trp Asn Tyr His Gly Gly Phe Arg Cys Tyr
                355                 360                 365

Pro Arg Asn Pro Cys Gln Asp Pro Tyr Ile Leu Thr Pro Glu Asn Arg
                370                 375                 380

Cys Val
385

<210> SEQ ID NO 2
<211> LENGTH: 378
<212> TYPE: PRT
<213> ORGANISM: Artificial sequence
<220> FEATURE:
<223> OTHER INFORMATION: Point mutated Homo sapiens

<400> SEQUENCE: 2

Met Leu Lys Ala Leu Phe Leu Thr Met Leu Thr Leu Ala Leu Val Lys
1               5                   10                  15

Ser Gln Asp Thr Glu Glu Thr Ile Thr Tyr Thr Gln Cys Thr Asp Gly
                20                  25                  30

Tyr Glu Trp Asp Pro Val Arg Gln Gln Cys Lys Asp Ile Asp Glu Cys
                35                  40                  45

Asp Ile Val Pro Asp Ala Cys Lys Gly Gly Met Lys Cys Val Asn His
            50                  55                  60

Tyr Gly Gly Tyr Leu Cys Leu Pro Lys Thr Ala Gln Ile Ile Val Asn
65                  70                  75                  80

Asn Glu Gln Pro Gln Gln Glu Thr Gln Pro Ala Glu Gly Thr Ser Gly
                85                  90                  95

Ala Thr Thr Gly Val Val Ala Ala Ser Ser Met Ala Thr Ser Gly Val
                100                 105                 110

Leu Pro Gly Gly Gly Phe Val Ala Ser Ala Ala Ala Val Ala Gly Pro
                115                 120                 125

Glu Met Gln Thr Gly Arg Asn Asn Phe Val Ile Arg Arg Asn Pro Ala
            130                 135                 140

Asp Pro Gln Arg Ile Pro Ser Asn Pro Ser His Arg Ile Gln Cys Ala
145                 150                 155                 160

Ala Gly Tyr Glu Gln Ser Glu His Asn Val Cys Gln Asp Ile Asp Glu
                165                 170                 175

Cys Thr Ala Gly Thr His Asn Cys Arg Ala Asp Gln Val Cys Ile Asn
                180                 185                 190

Leu Arg Gly Ser Phe Ala Cys Gln Cys Pro Pro Gly Tyr Gln Lys Arg
                195                 200                 205

Gly Asp Gln Cys Val Asp Ile Asp Glu Cys Thr Ile Pro Pro Tyr Cys
            210                 215                 220

His Gln Arg Cys Val Asn Thr Pro Gly Ser Phe Tyr Cys Gln Cys Ser
225                 230                 235                 240

Pro Gly Phe Gln Leu Ala Ala Asn Asn Tyr Thr Cys Val Asp Ile Asn
                245                 250                 255

Glu Cys Asp Ala Ser Asn Gln Cys Ala Gln Gln Cys Tyr Asn Ile Leu
                260                 265                 270

Gly Ser Phe Ile Cys Gln Cys Asn Gln Gly Tyr Glu Leu Ser Ser Asp
                275                 280                 285
```

```
Arg Leu Asn Cys Glu Asp Ile Asp Glu Cys Arg Thr Ser Ser Tyr Leu
    290                 295                 300
Cys Gln Tyr Gln Cys Val Asn Glu Pro Gly Lys Phe Ser Cys Met Cys
305                 310                 315                 320
Pro Gln Gly Tyr Gln Val Val Arg Ser Arg Thr Cys Gln Asp Ile Asn
                325                 330                 335
Glu Cys Glu Thr Thr Asn Glu Cys Arg Glu Asp Glu Met Cys Trp Asn
            340                 345                 350
Tyr His Gly Gly Phe Arg Cys Tyr Pro Arg Asn Pro Cys Gln Asp Pro
        355                 360                 365
Tyr Ile Leu Thr Pro Glu Asn Arg Cys Val
    370                 375
```

<210> SEQ ID NO 3
<211> LENGTH: 493
<212> TYPE: PRT
<213> ORGANISM: Artificial Sequence
<220> FEATURE:
<223> OTHER INFORMATION: Chemically Synthesized

<400> SEQUENCE: 3

```
Met Leu Lys Ala Leu Phe Leu Thr Met Leu Thr Leu Ala Leu Val Lys
1               5                   10                  15
Ser Gln Asp Thr Glu Glu Thr Ile Thr Tyr Thr Gln Cys Thr Asp Gly
                20                  25                  30
Tyr Glu Trp Asp Pro Val Arg Gln Gln Cys Lys Asp Ile Asp Glu Cys
            35                  40                  45
Asp Ile Val Pro Asp Ala Cys Lys Gly Gly Met Lys Cys Val Asn His
    50                  55                  60
Tyr Gly Gly Tyr Leu Cys Leu Pro Lys Thr Ala Gln Ile Ile Val Asn
65                  70                  75                  80
Asn Glu Gln Pro Gln Gln Glu Thr Gln Pro Ala Glu Gly Thr Ser Gly
                85                  90                  95
Ala Thr Thr Gly Val Val Ala Ala Ser Ser Met Ala Thr Ser Gly Val
                100                 105                 110
Leu Pro Gly Gly Phe Val Ala Ser Ala Ala Val Ala Gly Pro
            115                 120                 125
Glu Met Gln Thr Gly Arg Asn Asn Phe Val Ile Arg Arg Asn Pro Ala
130                 135                 140
Asp Pro Gln Arg Ile Pro Ser Asn Pro Ser His Arg Ile Gln Cys Ala
145                 150                 155                 160
Ala Gly Tyr Glu Gln Ser Glu His Asn Val Cys Gln Asp Ile Asp Glu
                165                 170                 175
Cys Thr Ala Gly Thr His Asn Cys Arg Ala Asp Gln Val Cys Ile Asn
            180                 185                 190
Leu Arg Gly Ser Phe Ala Cys Gln Cys Pro Pro Gly Tyr Gln Lys Arg
        195                 200                 205
Gly Glu Gln Cys Val Asp Ile Asp Glu Cys Thr Ile Pro Pro Tyr Cys
    210                 215                 220
His Gln Arg Cys Val Asn Thr Pro Gly Ser Phe Tyr Cys Gln Cys Ser
225                 230                 235                 240
Pro Gly Phe Gln Leu Ala Ala Asn Asn Tyr Thr Cys Val Asp Ile Asn
                245                 250                 255
Glu Cys Asp Ala Ser Asn Gln Cys Ala Gln Gln Cys Tyr Asn Ile Leu
            260                 265                 270
```

```
Gly Ser Phe Ile Cys Gln Cys Asn Gln Gly Tyr Glu Leu Ser Ser Asp
            275                 280                 285

Arg Leu Asn Cys Glu Asp Ile Asp Glu Cys Arg Thr Ser Ser Tyr Leu
    290                 295                 300

Cys Gln Tyr Gln Cys Val Asn Glu Pro Gly Lys Phe Ser Cys Met Cys
305                 310                 315                 320

Pro Gln Gly Tyr Gln Val Arg Ser Arg Thr Cys Gln Asp Ile Asn
                325                 330                 335

Glu Cys Glu Thr Thr Asn Glu Cys Arg Glu Asp Glu Met Cys Trp Asn
                340                 345                 350

Tyr His Gly Gly Phe Arg Cys Tyr Pro Arg Asn Pro Cys Gln Asp Pro
            355                 360                 365

Tyr Ile Leu Thr Pro Glu Asn Arg Cys Val Cys Pro Val Ser Asn Ala
        370                 375                 380

Met Cys Arg Glu Leu Pro Gln Ser Ile Val Tyr Lys Tyr Met Ser Ile
385                 390                 395                 400

Arg Ser Asp Arg Ser Val Pro Ser Asp Ile Phe Gln Ile Gln Ala Thr
                405                 410                 415

Thr Ile Tyr Ala Asn Thr Ile Asn Thr Phe Arg Ile Lys Ser Gly Asn
            420                 425                 430

Glu Asn Gly Glu Phe Tyr Leu Arg Gln Thr Ser Pro Val Ser Ala Met
        435                 440                 445

Leu Val Leu Val Lys Ser Leu Ser Gly Pro Arg Glu His Ile Val Asp
    450                 455                 460

Leu Glu Met Leu Thr Val Ser Ser Ile Gly Thr Phe Arg Thr Ser Ser
465                 470                 475                 480

Val Leu Arg Leu Thr Ile Ile Val Gly Pro Phe Ser Phe
                485                 490
```

```
<210> SEQ ID NO 4
<211> LENGTH: 443
<212> TYPE: PRT
<213> ORGANISM: Artificial Sequence
<220> FEATURE:
<223> OTHER INFORMATION: Chemically Synthesized

<400> SEQUENCE: 4

Met Leu Pro Cys Ala Ser Cys Leu Pro Gly Ser Leu Leu Leu Trp Ala
1               5                   10                  15

Leu Leu Leu Leu Leu Leu Gly Ser Ala Ser Pro Gln Asp Ser Glu Glu
            20                  25                  30

Pro Asp Ser Tyr Thr Glu Cys Thr Asp Gly Tyr Glu Trp Asp Pro Asp
        35                  40                  45

Ser Gln His Cys Arg Asp Val Asn Glu Cys Leu Thr Ile Pro Glu Ala
    50                  55                  60

Cys Lys Gly Glu Met Lys Cys Ile Asn His Tyr Gly Gly Tyr Leu Cys
65                  70                  75                  80

Leu Pro Arg Ser Ala Ala Val Ile Asn Asp Leu His Gly Glu Gly Pro
                85                  90                  95

Pro Pro Pro Val Pro Pro Ala Gln His Pro Asn Pro Cys Pro Pro Gly
            100                 105                 110

Tyr Glu Pro Asp Asp Gln Asp Ser Cys Val Asp Val Asp Glu Cys Ala
        115                 120                 125

Gln Ala Leu His Asp Cys Arg Pro Ser Gln Asp Cys His Asn Leu Pro
    130                 135                 140
```

```
Gly Ser Tyr Gln Cys Thr Cys Pro Asp Gly Tyr Arg Lys Ile Gly Pro
145                 150                 155                 160

Glu Cys Val Asp Ile Asp Glu Cys Arg Tyr Arg Tyr Cys Gln His Arg
                165                 170                 175

Cys Val Asn Leu Pro Gly Ser Phe Arg Cys Gln Cys Glu Pro Gly Phe
            180                 185                 190

Gln Leu Gly Pro Asn Asn Arg Ser Cys Val Asp Val Asn Glu Cys Asp
        195                 200                 205

Met Gly Ala Pro Cys Glu Gln Arg Cys Phe Asn Ser Tyr Gly Thr Phe
210                 215                 220

Leu Cys Arg Cys His Gln Gly Tyr Glu Leu His Arg Asp Gly Phe Ser
225                 230                 235                 240

Cys Ser Asp Ile Asp Glu Cys Ser Tyr Ser Ser Tyr Leu Cys Gln Tyr
                245                 250                 255

Arg Cys Val Asn Glu Pro Gly Arg Phe Ser Cys His Cys Pro Gln Gly
            260                 265                 270

Tyr Gln Leu Leu Ala Thr Arg Leu Cys Gln Asp Ile Asp Glu Cys Glu
        275                 280                 285

Ser Gly Ala His Gln Cys Ser Glu Ala Gln Thr Cys Val Asn Phe His
290                 295                 300

Gly Gly Tyr Arg Cys Val Asp Thr Asn Arg Cys Val Glu Pro Tyr Ile
305                 310                 315                 320

Gln Val Ser Glu Asn Arg Cys Leu Cys Pro Ala Ser Asn Pro Leu Cys
                325                 330                 335

Arg Glu Gln Pro Ser Ser Ile Val His Arg Tyr Met Thr Ile Thr Ser
            340                 345                 350

Glu Arg Ser Val Pro Ala Asp Val Phe Gln Ile Gln Ala Thr Ser Val
        355                 360                 365

Tyr Pro Gly Ala Tyr Asn Ala Phe Gln Ile Arg Ala Gly Asn Ser Gln
370                 375                 380

Gly Asp Phe Tyr Ile Arg Gln Ile Asn Asn Val Ser Ala Met Leu Val
385                 390                 395                 400

Leu Ala Arg Pro Val Thr Gly Pro Arg Glu Tyr Val Leu Asp Leu Glu
                405                 410                 415

Met Val Thr Met Asn Ser Leu Met Ser Tyr Arg Ala Ser Ser Val Leu
            420                 425                 430

Arg Leu Thr Val Phe Val Gly Ala Tyr Thr Phe
        435                 440

<210> SEQ ID NO 5
<211> LENGTH: 448
<212> TYPE: PRT
<213> ORGANISM: Artificial Sequence
<220> FEATURE:
<223> OTHER INFORMATION: Chemically Synthesized

<400> SEQUENCE: 5

Met Pro Gly Ile Lys Arg Ile Leu Thr Val Thr Ile Leu Ala Leu Cys
1               5                   10                  15

Leu Pro Ser Pro Gly Asn Ala Gln Ala Gln Cys Thr Asn Gly Phe Asp
            20                  25                  30

Leu Asp Arg Gln Ser Gly Gln Cys Leu Asp Ile Asp Glu Cys Arg Thr
        35                  40                  45

Ile Pro Glu Ala Cys Arg Gly Asp Met Met Cys Val Asn Gln Asn Gly
50                  55                  60
```

```
Gly Tyr Leu Cys Ile Pro Arg Thr Asn Pro Val Tyr Arg Gly Pro Tyr
 65                  70                  75                  80

Ser Asn Pro Tyr Ser Thr Pro Tyr Ser Gly Pro Tyr Pro Ala Ala Ala
                 85                  90                  95

Pro Pro Leu Ser Ala Pro Asn Tyr Pro Thr Ile Ser Arg Pro Leu Ile
            100                 105                 110

Cys Arg Phe Gly Tyr Gln Met Asp Glu Ser Asn Gln Cys Val Asp Val
        115                 120                 125

Asp Glu Cys Ala Thr Asp Ser His Gln Cys Asn Pro Thr Gln Ile Cys
130                 135                 140

Ile Asn Thr Glu Gly Gly Tyr Thr Cys Ser Cys Thr Asp Gly Tyr Trp
145                 150                 155                 160

Leu Leu Glu Gly Gln Cys Leu Asp Ile Asp Glu Cys Arg Tyr Gly Tyr
                165                 170                 175

Cys Gln Gln Leu Cys Ala Asn Val Pro Gly Ser Tyr Ser Cys Thr Cys
            180                 185                 190

Asn Pro Gly Phe Thr Leu Asn Glu Asp Gly Arg Ser Cys Gln Asp Val
        195                 200                 205

Asn Glu Cys Ala Thr Glu Asn Pro Cys Val Gln Thr Cys Val Asn Thr
210                 215                 220

Tyr Gly Ser Phe Ile Cys Arg Cys Asp Pro Gly Tyr Glu Leu Glu Glu
225                 230                 235                 240

Asp Gly Val His Cys Ser Asp Met Asp Glu Cys Ser Phe Ser Glu Phe
                245                 250                 255

Leu Cys Gln His Glu Cys Val Asn Gln Pro Gly Thr Tyr Phe Cys Ser
            260                 265                 270

Cys Pro Pro Gly Tyr Ile Leu Leu Asp Asp Asn Arg Ser Cys Gln Asp
        275                 280                 285

Ile Asn Glu Cys Glu His Arg Asn His Thr Cys Asn Leu Gln Gln Thr
290                 295                 300

Cys Tyr Asn Leu Gln Gly Gly Phe Lys Cys Ile Asp Pro Ile Arg Cys
305                 310                 315                 320

Glu Glu Pro Tyr Leu Arg Ile Ser Asp Asn Arg Cys Met Cys Pro Ala
                325                 330                 335

Glu Asn Pro Gly Cys Arg Asp Gln Pro Phe Thr Ile Leu Tyr Arg Asp
            340                 345                 350

Met Asp Val Val Ser Gly Arg Ser Val Pro Ala Asp Ile Phe Gln Met
        355                 360                 365

Gln Ala Thr Thr Arg Tyr Pro Gly Ala Tyr Tyr Ile Phe Gln Ile Lys
370                 375                 380

Ser Gly Asn Glu Gly Arg Glu Phe Tyr Met Arg Gln Thr Gly Pro Ile
385                 390                 395                 400

Ser Ala Thr Leu Val Met Thr Arg Pro Ile Lys Gly Pro Arg Glu Ile
                405                 410                 415

Gln Leu Asp Leu Glu Met Ile Thr Val Asn Thr Val Ile Asn Phe Arg
            420                 425                 430

Gly Ser Ser Val Ile Arg Leu Arg Ile Tyr Val Ser Gln Tyr Pro Phe
        435                 440                 445

<210> SEQ ID NO 6
<211> LENGTH: 60
<212> TYPE: PRT
<213> ORGANISM: Homo sapiens

<400> SEQUENCE: 6
```

-continued

```
Gln Gln Glu Thr Gln Pro Ala Glu Gly Thr Ser Gly Ala Thr Thr Gly
1               5                   10                  15

Val Val Ala Ala Ser Ser Met Ala Thr Ser Gly Val Leu Pro Gly Gly
            20                  25                  30

Gly Phe Val Ala Ser Ala Ala Val Ala Gly Pro Glu Met Gln Thr
        35                  40                  45

Gly Arg Asn Asn Phe Val Ile Arg Arg Asn Pro Ala
    50                  55                  60

<210> SEQ ID NO 7
<211> LENGTH: 38
<212> TYPE: PRT
<213> ORGANISM: Mus musculus

<400> SEQUENCE: 7

Met Ala Thr Ser Gly Val Val Pro Gly Gly Gly Phe Met Ala Ser Ala
1               5                   10                  15

Thr Ala Val Ala Gly Pro Glu Val Gln Thr Gly Arg Asn Asn Phe Val
            20                  25                  30

Ile Arg Arg Asn Pro Ala
        35

<210> SEQ ID NO 8
<211> LENGTH: 38
<212> TYPE: PRT
<213> ORGANISM: Rattus norvegicus

<400> SEQUENCE: 8

Met Ala Thr Ser Gly Val Ile Pro Gly Gly Gly Phe Ile Ala Ser Ala
1               5                   10                  15

Thr Ala Val Ala Gly Pro Glu Val Gln Thr Gly Arg Asn Asn Phe Val
            20                  25                  30

Ile Arg Arg Asn Pro Ala
        35

<210> SEQ ID NO 9
<211> LENGTH: 68
<212> TYPE: PRT
<213> ORGANISM: Homo sapiens

<400> SEQUENCE: 9

Thr Thr Tyr Gln Met Asp Val Asn Pro Glu Gly Lys Tyr Ser Phe Gly
1               5                   10                  15

Ala Thr Cys Val Lys Lys Cys Pro Arg Asn Tyr Val Val Thr Asp His
            20                  25                  30

Gly Ser Cys Val Arg Ala Cys Gly Ala Asp Ser Tyr Glu Met Glu Glu
        35                  40                  45

Asp Gly Val Arg Lys Cys Lys Lys Cys Glu Gly Pro Cys Arg Lys Val
    50                  55                  60

Cys Asn Gly Ile
65

<210> SEQ ID NO 10
<211> LENGTH: 68
<212> TYPE: PRT
<213> ORGANISM: Homo sapiens

<400> SEQUENCE: 10

Thr Thr Tyr Gln Met Asp Val Asn Pro Glu Gly Lys Tyr Ser Phe Gly
```

-continued

```
                1               5                  10                 15
             Ala Thr Cys Val Lys Lys Cys Pro Arg Asn Tyr Val Val Thr Asp His
                              20                 25                 30

Gly Ser Cys Val Arg Ala Cys Gly Ala Asp Ser Tyr Glu Met Glu Glu
                       35                 40                 45

Asp Gly Val Arg Lys Cys Lys Lys Cys Glu Gly Pro Cys Arg Lys Val
                  50                 55                 60

Cys Asn Gly Ile
              65

<210> SEQ ID NO 11
<211> LENGTH: 68
<212> TYPE: PRT
<213> ORGANISM: Homo sapiens

<400> SEQUENCE: 11

Thr Thr Tyr Gln Met Asp Val Asn Pro Glu Gly Lys Tyr Ser Phe Gly
 1               5                  10                 15

Ala Thr Cys Val Lys Lys Cys Pro Arg Asn Tyr Val Val Thr Asp His
                  20                 25                 30

Gly Ser Cys Val Arg Ala Cys Gly Ala Asp Ser Tyr Glu Met Glu Glu
          35                 40                 45

Asp Gly Val Arg Lys Cys Lys Lys Cys Glu Gly Pro Cys Arg Lys Val
     50                 55                 60

Cys Asn Gly Ile
 65

<210> SEQ ID NO 12
<211> LENGTH: 68
<212> TYPE: PRT
<213> ORGANISM: Homo sapiens

<400> SEQUENCE: 12

Thr Thr Tyr Gln Met Asp Val Asn Pro Glu Gly Lys Tyr Ser Phe Gly
 1               5                  10                 15

Ala Thr Cys Val Lys Lys Cys Pro Arg Asn Tyr Val Val Thr Asp His
                  20                 25                 30

Gly Ser Cys Val Arg Ala Cys Gly Ala Asp Ser Tyr Glu Met Glu Glu
          35                 40                 45

Asp Gly Val Arg Lys Cys Lys Lys Cys Glu Gly Pro Cys Arg Lys Val
     50                 55                 60

Cys Asn Gly Ile
 65

<210> SEQ ID NO 13
<211> LENGTH: 45
<212> TYPE: PRT
<213> ORGANISM: Homo sapiens

<400> SEQUENCE: 13

Lys Gly Asn Tyr Val Val Thr Asp His Gly Ser Cys Val Arg Ala Cys
 1               5                  10                 15

Gly Ala Asp Ser Tyr Glu Met Glu Glu Asp Gly Val Arg Lys Cys Lys
                  20                 25                 30

Lys Cys Glu Gly Pro Cys Arg Lys Val Cys Asn Gly Ile
          35                 40                 45

<210> SEQ ID NO 14
```

<211> LENGTH: 351
<212> TYPE: PRT
<213> ORGANISM: Artificial Sequence
<220> FEATURE:
<223> OTHER INFORMATION: Amino acid sequence of ZR30 protein

<400> SEQUENCE: 14

```
Gln Cys Thr Asp Gly Tyr Glu Trp Asp Pro Val Arg Gln Gln Cys Lys
1               5                   10                  15

Asp Ile Asp Glu Cys Asp Ile Val Pro Asp Ala Cys Lys Gly Gly Met
            20                  25                  30

Lys Cys Val Asn His Tyr Gly Gly Tyr Leu Cys Leu Pro Lys Thr Ala
        35                  40                  45

Gln Ile Ile Val Asn Asn Glu Gln Pro Gln Gln Glu Thr Gln Pro Ala
    50                  55                  60

Glu Gly Thr Ser Gly Ala Thr Thr Gly Val Val Ala Ala Ser Ser Met
65                  70                  75                  80

Ala Thr Ser Gly Val Leu Pro Gly Gly Phe Val Ala Ser Ala Ala
                85                  90                  95

Ala Val Ala Gly Pro Glu Met Gln Thr Gly Arg Asn Asn Phe Val Ile
            100                 105                 110

Arg Arg Asn Pro Ala Asp Pro Gln Arg Ile Pro Ser Asn Pro Ser His
        115                 120                 125

Arg Ile Gln Cys Ala Ala Gly Tyr Glu Gln Ser Glu His Asn Val Cys
130                 135                 140

Gln Asp Ile Asp Glu Cys Thr Ala Gly Thr His Asn Cys Arg Ala Asp
145                 150                 155                 160

Gln Val Cys Ile Asn Leu Arg Gly Ser Phe Ala Cys Gln Cys Pro Pro
            165                 170                 175

Gly Tyr Gln Lys Arg Gly Asp Gln Cys Val Asp Ile Asp Glu Cys Thr
        180                 185                 190

Ile Pro Pro Tyr Cys His Gln Arg Cys Val Asn Thr Pro Gly Ser Phe
    195                 200                 205

Tyr Cys Gln Cys Ser Pro Gly Phe Gln Leu Ala Ala Asn Asn Tyr Thr
210                 215                 220

Cys Val Asp Ile Asn Glu Cys Asp Ala Ser Asn Gln Cys Ala Gln Gln
225                 230                 235                 240

Cys Tyr Asn Ile Leu Gly Ser Phe Ile Cys Gln Cys Asn Gln Gly Tyr
            245                 250                 255

Glu Leu Ser Ser Asp Arg Leu Asn Cys Glu Asp Ile Asp Glu Cys Arg
        260                 265                 270

Thr Ser Ser Tyr Leu Cys Gln Tyr Gln Cys Val Asn Glu Pro Gly Lys
    275                 280                 285

Phe Ser Cys Met Cys Pro Gln Gly Tyr Gln Val Val Arg Ser Arg Thr
290                 295                 300

Cys Gln Asp Ile Asn Glu Cys Glu Thr Asn Glu Cys Arg Glu Asp
305                 310                 315                 320

Glu Met Cys Trp Asn Tyr His Gly Gly Phe Arg Cys Tyr Pro Arg Asn
            325                 330                 335

Pro Cys Gln Asp Pro Tyr Ile Leu Thr Pro Glu Asn Arg Cys Val
        340                 345                 350
```

<210> SEQ ID NO 15
<211> LENGTH: 21
<212> TYPE: DNA
<213> ORGANISM: Artificial Sequence

```
-continued

<220> FEATURE:
<223> OTHER INFORMATION: Nucleotide Primer sequence for human SPAG16 (1)

<400> SEQUENCE: 15
gcaagtggca atggtgttat c                                              21

<210> SEQ ID NO 16
<211> LENGTH: 21
<212> TYPE: DNA
<213> ORGANISM: Artificial Sequence
<220> FEATURE:
<223> OTHER INFORMATION: Nucleotide Primer sequence for human SPAG16 (2)

<400> SEQUENCE: 16
gctggcacat ttaaccagtt c                                              21

<210> SEQ ID NO 17
<211> LENGTH: 20
<212> TYPE: DNA
<213> ORGANISM: Artificial Sequence
<220> FEATURE:
<223> OTHER INFORMATION: Nucleotide Primer sequence for mouse SPAG16 (1)

<400> SEQUENCE: 17
agccatcttc aacagagtcc                                                20

<210> SEQ ID NO 18
<211> LENGTH: 20
<212> TYPE: DNA
<213> ORGANISM: Artificial Sequence
<220> FEATURE:
<223> OTHER INFORMATION: Nucleotide Primer sequence for mouse SPAG16 (2)

<400> SEQUENCE: 18
ctctcttgtg ctaatggagc                                                20

<210> SEQ ID NO 19
<211> LENGTH: 18
<212> TYPE: DNA
<213> ORGANISM: Artificial Sequence
<220> FEATURE:
<223> OTHER INFORMATION: Nucleotide Primer sequence for GFP in
      pGIPZ-Vector (1)

<400> SEQUENCE: 19
atggagagcg acgagagc                                                  18

<210> SEQ ID NO 20
<211> LENGTH: 20
<212> TYPE: DNA
<213> ORGANISM: Artificial Sequence
<220> FEATURE:
<223> OTHER INFORMATION: Nucleotide Primer sequence for GFP in
      pGIPZ-Vector (2)

<400> SEQUENCE: 20
cgcctttggt gctcttcatc                                                20

<210> SEQ ID NO 21
<211> LENGTH: 21
<212> TYPE: DNA
<213> ORGANISM: Artificial Sequence
<220> FEATURE:
<223> OTHER INFORMATION: Nucleotide Primer sequence for GFP in RFP in
      pTRIPZ (1)

<400> SEQUENCE: 21
```

```
aggagaacat gcacatgaag c                                             21

<210> SEQ ID NO 22
<211> LENGTH: 20
<212> TYPE: DNA
<213> ORGANISM: Artificial Sequence
<220> FEATURE:
<223> OTHER INFORMATION: Nucleotide Primer sequence for GFP in RFP in
      pTRIPZ (2)

<400> SEQUENCE: 22
gccgtacatg aagctggtag                                               20

<210> SEQ ID NO 23
<211> LENGTH: 1053
<212> TYPE: DNA
<213> ORGANISM: Artificial Sequence
<220> FEATURE:
<223> OTHER INFORMATION: Nucleotide sequence for ZR30

<400> SEQUENCE: 23
caatgcactg acggatatga gtgggatcct gtgagacagc aatgcaaaga tattgatgaa    60
tgtgacattg tcccagacgc ttgtaaaggt ggaatgaagt gtgtcaacca ctatggagga   120
tacctctgcc ttccgaaaac agcccagatt attgtcaata atgaacagcc tcagcaggaa   180
acacaaccag cagaaggaac ctcaggggca accaccgggg ttgtagctgc cagcagcatg   240
gcaaccagtg gagtgttgcc cggggggtggt tttgtggcca gtgctgctgc agtcgcaggc   300
cctgaaatgc agactggccg aaataacttt gtcatccggc ggaacccagc tgaccctcag   360
cgcattccct ccaacccttc ccaccgtatc cagtgtgcag caggctacga gcaaagtgaa   420
cacaacgtgt gccaagacat agacgagtgc actgcaggga cgcacaactg tagagcagac   480
caagtgtgca tcaatttacg gggatccttt gcatgtcagt gccctcctgg atatcagaag   540 cgagggacc agtgcgtaga catagatgaa tgtaccatcc ctccatattg ccaccaaaga   600
tgcgtgaata caccaggctc attttattgc cagtgcagtc ctgggtttca attggcagca   660
aacaactata cctgcgtaga tataaatgaa tgtgatgcca gcaatcaatg tgctcagcag   720
tgctacaaca ttcttggttc attcatctgt cagtgcaatc aaggatatga gctaagcagt   780
gacaggctca actgtgaaga cattgatgaa tgcagaacct caagctacct gtgtcaatat   840
caatgtgtca atgaacctgg gaaattctca tgtatgtgcc cccagggata ccaagtggtg   900
agaagtagaa catgtcaaga tataaatgag tgtgagacca caaatgaatg ccgggaggat   960
gaaatgtgtt ggaattatca tggcggcttc cgttgttatc cacgaaatcc ttgtcaagat  1020
ccctacattc taacaccaga gaaccgatgt gtt                              1053
```